(12) United States Patent
Maley

(10) Patent No.: US 6,595,035 B1
(45) Date of Patent: Jul. 22, 2003

(54) SEALANT STREAM ANOMALY DETECTING ASSEMBLY

(75) Inventor: Myron G. Maley, Pontiac, MI (US)

(73) Assignee: Jesco Products Company, Inc., Sterling Heights, MI (US)

( * ) Notice: Subject to any disclaimer, the term of this patent is extended or adjusted under 35 U.S.C. 154(b) by 64 days.

(21) Appl. No.: 09/849,677

(22) Filed: May 4, 2001

Related U.S. Application Data

(60) Provisional application No. 60/201,952, filed on May 5, 2000.

(51) Int. Cl.$^7$ .................. G01N 29/02; G01N 7/00
(52) U.S. Cl. ............ 73/19.03; 73/64.53; 73/599; 73/602; 340/627
(58) Field of Search ............ 73/19.03, 64.53, 73/599, 602; 340/627

(56) References Cited

U.S. PATENT DOCUMENTS

| | | | | |
|---|---|---|---|---|
| 4,235,095 A | * | 11/1980 | Liebermann | 73/19.03 |
| 4,607,520 A | * | 8/1986 | Dam | 73/19.03 |
| 5,811,659 A | * | 9/1998 | Giebler | 73/19.03 |
| 6,012,324 A | * | 1/2000 | Jakkula et al. | 73/19.03 |
| 6,142,008 A | * | 11/2000 | Cole et al. | 73/19.03 |
| 6,401,538 B1 | * | 6/2002 | Han et al. | 73/599 |
| 6,408,679 B1 | * | 6/2002 | Kline-Schoder et al. | 73/19.03 |
| 6,467,331 B1 | * | 10/2002 | Kline-Schoder et al. | 73/19.03 |

* cited by examiner

*Primary Examiner*—Helen Kwok
*Assistant Examiner*—David J. Wiggins
(74) *Attorney, Agent, or Firm*—Reising, Ethington, Barnes, Kisselle, P.C.

(57) ABSTRACT

A sealant stream anomaly detecting assembly for detecting anomalies such as gas bubbles in a high-pressure sealant stream. The assembly includes an ultrasonic transducer supported on a manifold defining a sensing chamber of a fluid channel. The transducer converts electrical voltage pulses into ultrasonic acoustic pulses and propagates the acoustic pulses through the manifold and into the sensing chamber. The transducer also receives resulting echo pulses from a back wall of the sensing chamber and converts the echo pulses into electrical output impulses. A control module including drive electronics is connected to the transducer. The module detects diminished and lost echo pulses by comparing the output impulse strength values for a given fluid passing through the sensing chamber to a known output impulse strength value for that same type of fluid having no anomalies. An anomaly indicator connected to the control module flags a user when module detects a bubble or other anomaly in a fluid stream passing through the fluid channel. The transducer has a flat front emitter surface that lies flat against a flat manifold outer surface to provide superior acoustic energy pulse coverage throughout the sensing chamber.

37 Claims, 21 Drawing Sheets

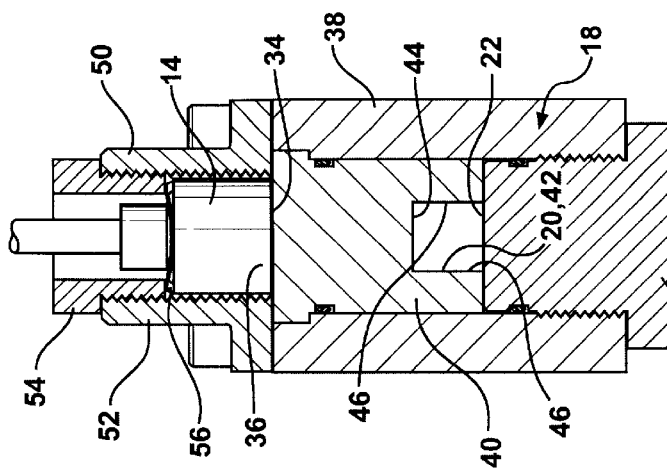
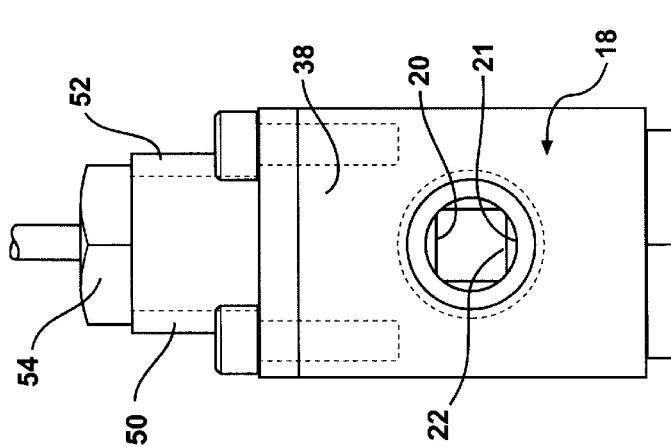
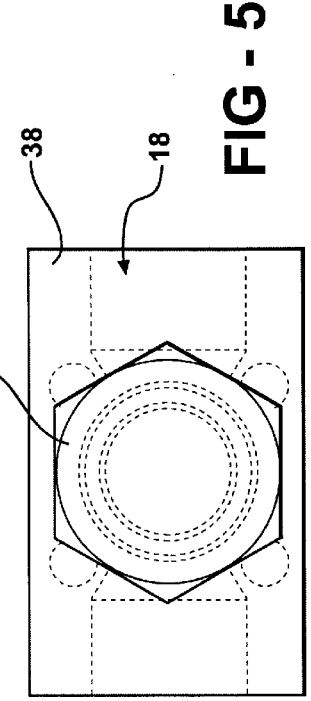
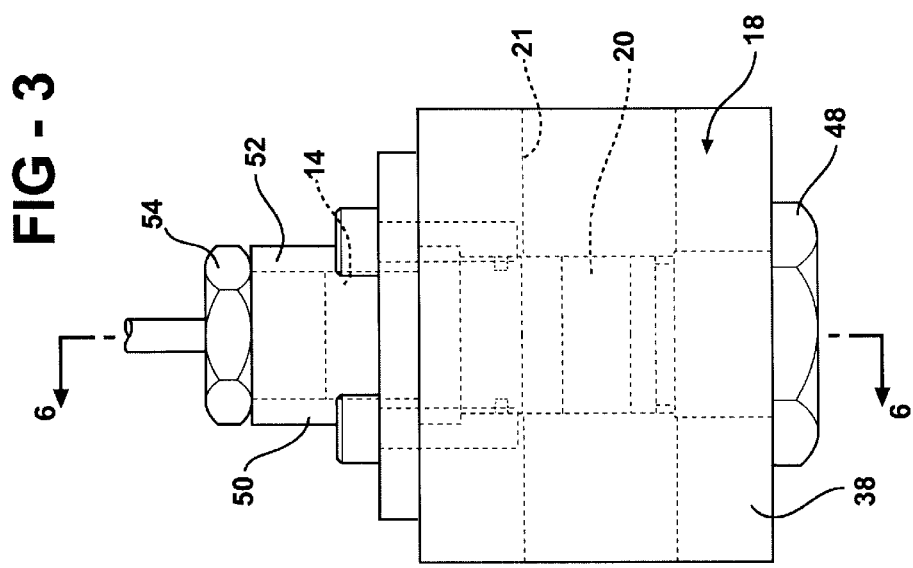

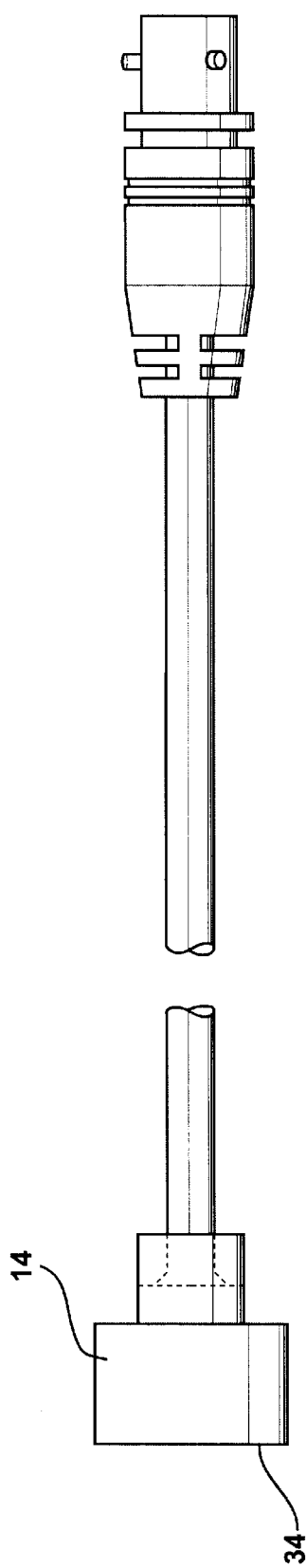
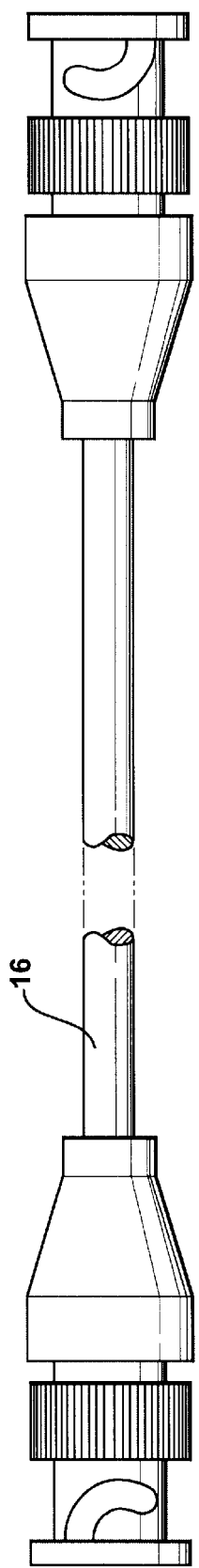
FIG - 7
FIG - 8

SEALANT STREAM ANOMALY DETECTING ASSEMBLY

CROSS-REFERENCES TO RELATED APPLICATIONS

This application claims the benefit of provisional application Ser. No. 60/201,952, filed May 5, 2000.

STATEMENT REGARDING FEDERALLY SPONSORED RESEARCH OR DEVELOPMENT

Not Applicable

BACKGROUND OF THE INVENTION

1. Field of the Invention

This invention relates generally to sealant stream anomaly detecting assembly for detecting gas bubbles and solid contaminants (such as cured material) in a high-pressure sealant stream.

2. Description of the Related Art Including Information Disclosed Under 37 CFR 1.97 and 1.98

It is known for a liquid stream bubble detecting assembly to include an ultrasonic transducer supported adjacent a liquid channel. In such assemblies the ultrasonic transducer is configured to emit ultrasonic sound energy pulses into a portion of the channel and to convert returning echo pulses into electrical impulses. These electrical impulses are proportional in strength to the amount of sound energy returned in the echo pulses.

Ultrasonic imaging or comparison is affected by the fact that different materials exhibit different acoustic properties. When mixed, different materials can be sampled in contrast to each other by the variations in both propagation velocity and shunt energy absorption that they exhibit as acoustic energy propagates through them. These differences in propagation and absorption can have a dramatic affect on the amplitude of return echoes. These variations in echo amplitude make it possible to discriminate between a uniform fluid medium and any anomalous, non-uniformities.

Liquids, for example, are relatively dense. Partly for this reason, liquids allow a relatively large amount of sound energy to echo back to an emitting transducer. Gasses on the other hand, partly because they are less dense than liquids, absorb most of the sound waves emitted by a transducer. Liquids containing bubbles are less dense than liquids having no bubbles and consequently absorb more sound waves than liquids having no bubbles.

Liquid stream bubble detecting assemblies are known to include drive electronics that are connected to the transducers of such assemblies and are calibrated to detect diminished or lost echo pulses. Drive electronics detect diminished or lost echo pulses in a given liquid by comparing the strength of the echo pulses to known signal strength levels encountered when ultrasonic sound energy is transmitted and echoed back through that given liquid when the liquid is bubble-free.

It is also known for liquid stream bubble detecting assemblies to include bubble indicators configured to flag a user that the assembly has detected a bubble in a liquid stream passing through the liquid channel.

For example, ultrasonic bubble detector assemblies are known to be used in detecting air bubbles in streams of blood flowing through blood transfusion pumps. One such system includes an ultrasonic transducer that is optimized for such medical applications and is supported adjacent a channel that carries blood through the transfusion pump. However, a blood transfusion pump bubble sensor assembly of this type would be unlikely to detect gas bubbles in a high-pressure stream of liquid sealant or to be able to withstand the high pressure or abrasive nature of a sealant stream.

In addition, ultrasonic bubble detecting assemblies are known to be used in detecting cavitation bubbles in hydraulic liquid flowing through a hydraulic system. However, a liquid stream bubble detecting assembly of this type would be unlikely to reliably detect gas bubbles in a high-pressure stream of liquid sealant or to be able to withstand an abrasive sealant stream.

What is needed is a liquid stream anomaly detecting assembly that can detect gas bubbles and/or solids in a stream of liquid sealant without failing due to the high pressures involved and the abrasive effect of sealant streams. What is also needed is such an assembly that is designed and built to work reliably in an industrial environment that subjects the assembly to such factors as electrical noise, temperature changes, vibration, motion and a variety of sealant materials to be inspected for bubbles and/or immersed solids. To be adaptable to such an environment it is also desirable that such an assembly be easy to repeatedly adjust and calibrate.

BRIEF SUMMARY OF THE INVENTION

The invention is a sealant stream anomaly detecting assembly for detecting gas bubbles, immersed solids such as cured sealant and foreign objects, and/or other such anomalies in a high-pressure sealant stream. The assembly includes an ultrasonic transducer supported on a manifold defining a sensing chamber portion of a fluid channel. The transducer is configured to convert electrical input voltage pulses into ultrasonic acoustic energy pulses and to propagate the acoustic energy pulses through the manifold and into the sensing chamber. The transducer is also configured to receive resulting echo pulses from a back wall of the sensing chamber and to convert the echo pulses into electrical output impulses. An electronics module includes drive electronics connected to the transducer. The module is configured to receive the electrical output impulses from the transducer and to detect diminished and lost echo pulses by comparing the output impulse strength values for a given fluid passing through the sensing chamber to a known output impulse strength value for that same type of fluid having no bubbles or immersed solids. The sealant stream anomaly detecting assembly also includes an anomaly indicator connected to the electronics module and configured to flag a user in response to a signal from the electronics module indicating that the assembly has detected a bubble in a fluid stream passing through the fluid channel.

The transducer has a flat front emitter surface that lies flat against a flat manifold outer surface to provide superior acoustic energy pulse coverage throughout the sensing chamber. Increased pulse coverage results in improved anomaly detecting ability.

The invention also includes a method for detecting gas bubbles or immersed solids in a high-pressure sealant stream. According to this method one can detect gas bubbles or immersed solids in a high-pressure sealant stream by providing a sensing chamber in a fluid channel, providing an ultrasonic transducer, associated drive electronics and sensing chamber, connecting the ultrasonic transducer and associated drive electronics to the sensing chamber and connecting the anomaly indicator to the drive electronics. A fluid to be inspected for the presence of bubbles or immersed solids is then passed through the sensing chamber and the drive electronics are actuated to operate the transducer and detect bubbles or immersed solids in the fluid passing through the sensing chamber. The anomaly indicator is actuated to indicate to an operator and/or supervisory controller when the transducer and drive electronics detect a bubble in the fluid passing through the sensing chamber.

BRIEF DESCRIPTION OF THE SEVERAL VIEWS OF THE DRAWINGS

These and other features and advantages of the invention will become apparent to those skilled in the art in connection with the following detailed description and drawings, in which:

FIG. 3 is a front view of the manifold assembly of FIG. 2;

FIG. 4 is a side view of the manifold assembly of FIG. 2;

FIG. 5 is a bottom view of the manifold assembly of FIG. 2;

FIG. 6 is a partial cross-sectional view of the manifold assembly of FIG. 2 taken along line A—A of FIG. 3 and showing the position of an ultrasonic transducer of the assembly;

FIG. 7 is a front view of an ultrasonic transducer and integral pigtail connector of the manifold assembly of FIG. 2;

FIG. 8 is a front view of a typical coaxial cable construction for the bubble detection assembly of FIG. 1;

DETAILED DESCRIPTION OF INVENTION EMBODIMENT(S)

Figure 1:
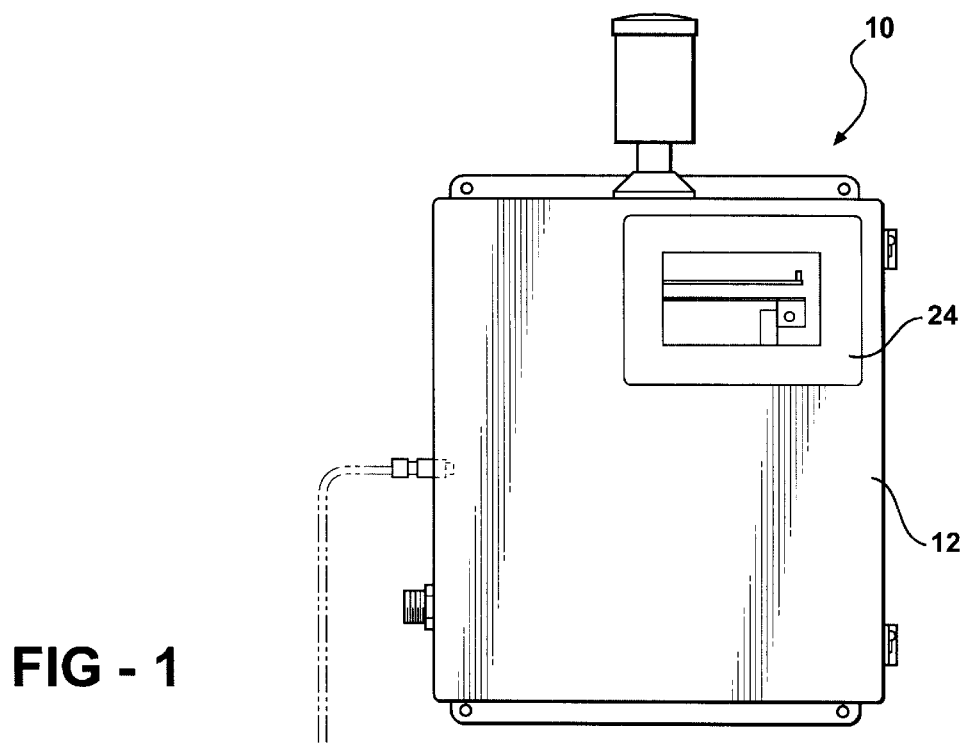
FIG. 1 is a front view of a bubble detection assembly constructed according to the invention.
Figure 2:
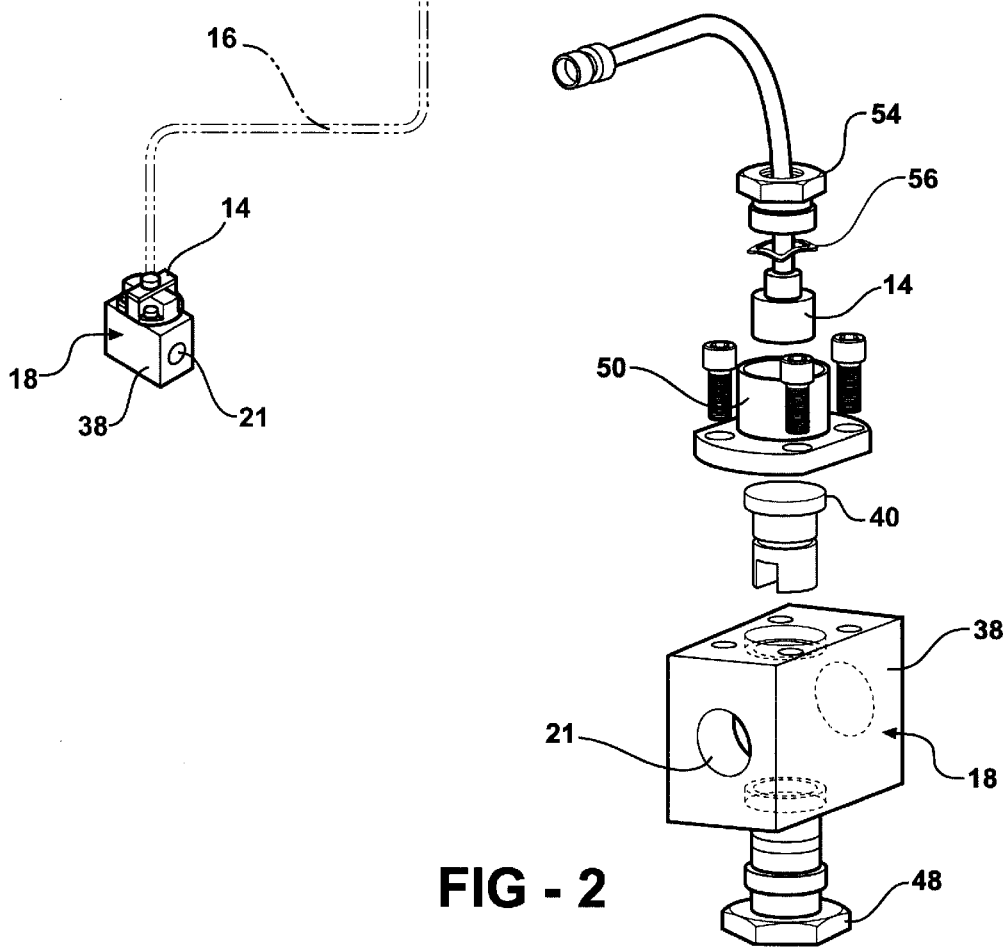
FIG. 2 is an exploded, perspective view of a manifold assembly of the bubble detection assembly of FIG. 1.
Figure 9:
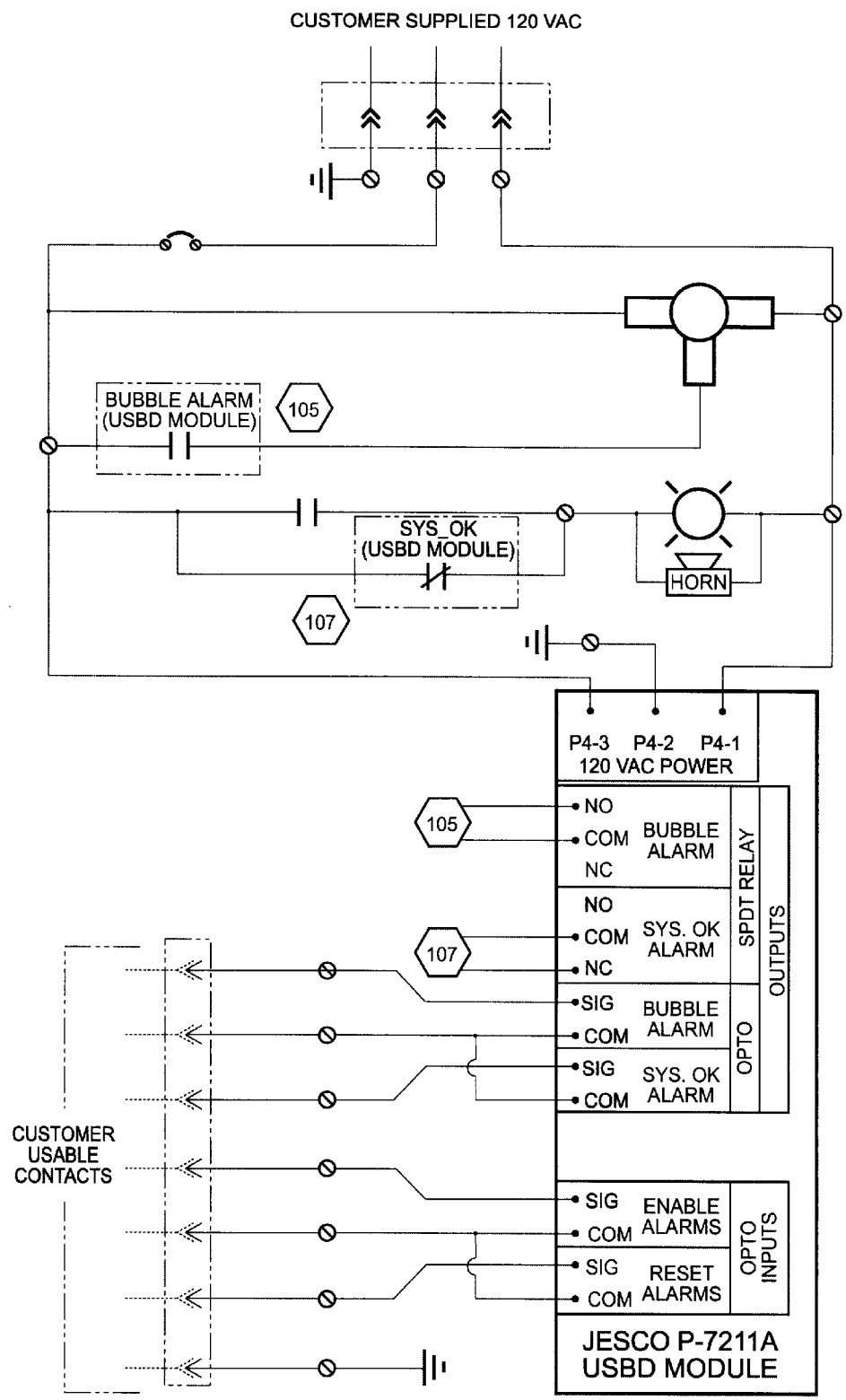
FIG. 9 is a schematic diagram of a control panel assembly of the bubble detection assembly of FIG. 1.
Figure 10:
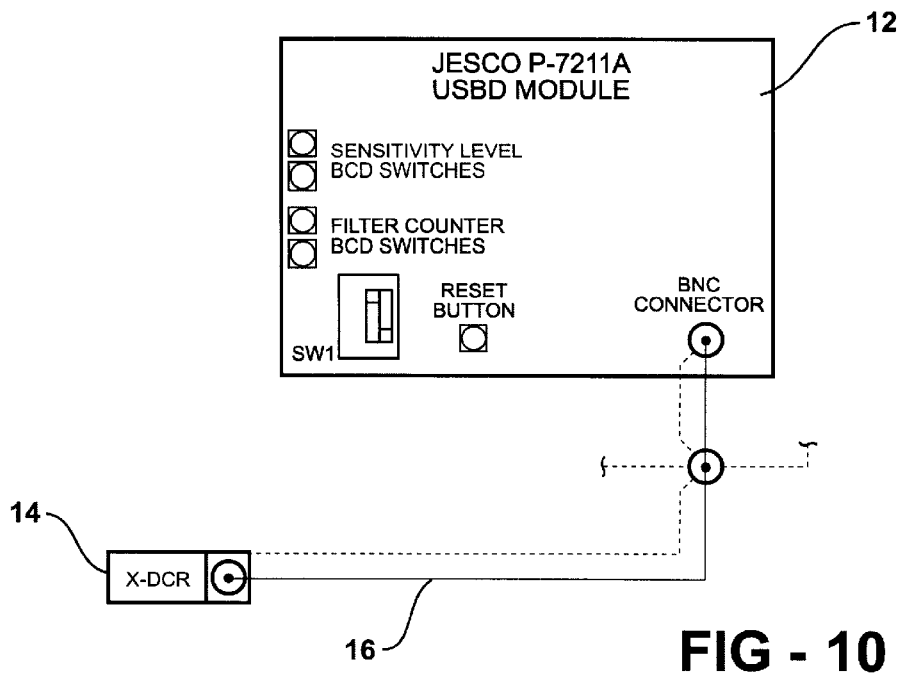
FIG. 10 is a schematic face view of the coaxial cables connecting the transducer to the control panel assembly.
Figure 11:
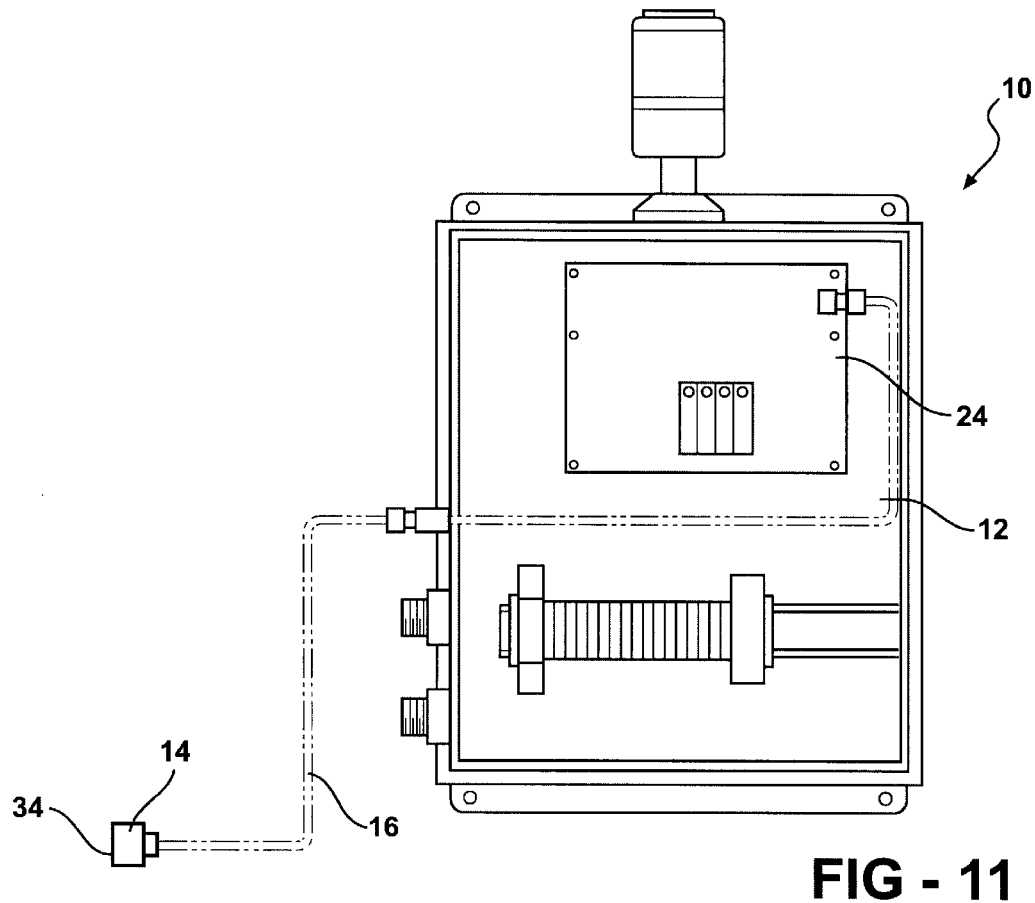
FIG. 11 is a front view of the control panel assembly of the bubble detection assembly of FIG. 1 with a front cover of the panel removed.
Figure 12:
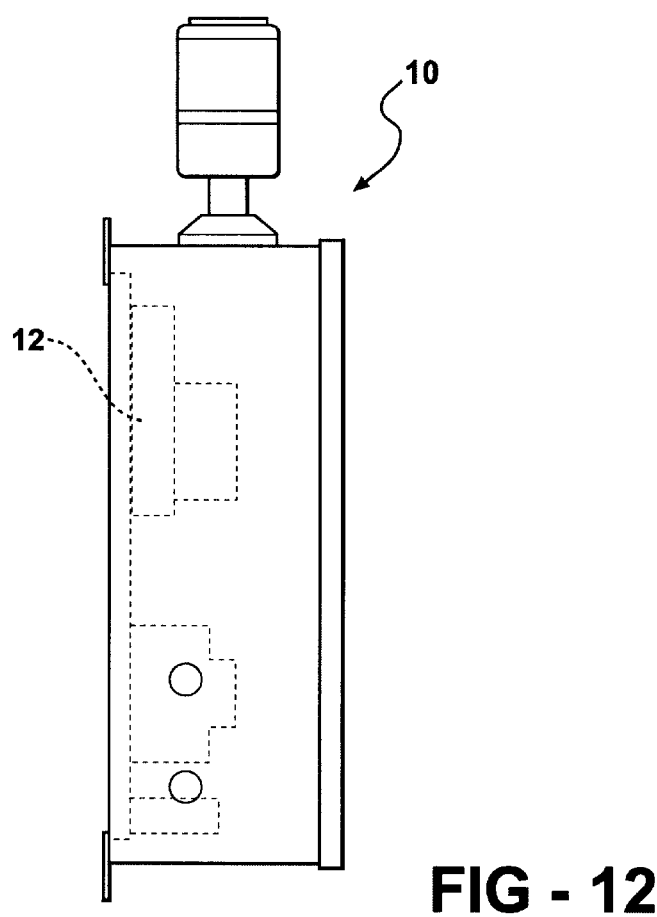
FIG. 12 is a side view of the control panel assembly of FIG. 10 with hidden interior component locations shown.
Figure 13:
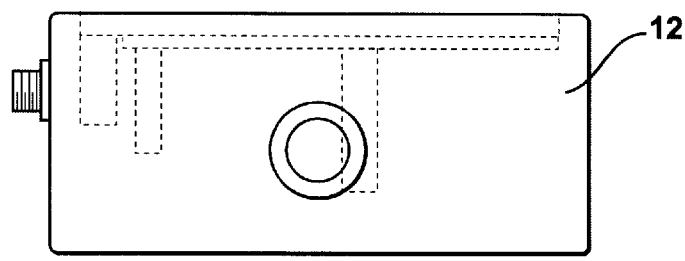
FIG. 13 is a plan view of the control panel assembly of FIG. 10 with hidden interior component locations shown.

A sealant stream anomaly detecting assembly for detecting gas bubbles and other anomalies in a high-pressure sealant stream is shown at 10 in the Figures. While the present embodiment is optimized for bubble detection, other embodiments may be optimized to detect other anomalies such as immersed solids. The assembly 10 includes a small control panel 12 and a remote ultrasonic transducer 14 mounted to a fluid manifold 18. A 50 foot coaxial cable 16 connects the transducer 14 to the control panel 12. The fluid manifold 18 defines a sensing chamber portion 20 of a fluid channel 21.

The transducer 14 converts electrical input voltage pulses into ultrasonic acoustic energy pulses and propagates the acoustic energy pulses through the manifold 18 and into the sensing chamber 20. Once the acoustic waves have entered the sensing chamber 20, they propagate through the fluid if there are no density differences present then are reflected back from a steel faced back wall 22 of the fluid manifold 18. The transducer 14 receives the resulting echo pulses from the back wall 22 of the sensing chamber 20 and converts the echo pulses into electrical output impulses.

The control panel 12 includes an electronic control module 24 designed to operate the system, control its functions and allow customer interface and adjustments for setting the system up to suit their needs. The control panel 12 also includes audio, visual and user alarm (electrical) outputs that can easily be seen and heard by personnel and/or used by other automated equipment for the purposes of fault monitoring.

The control module 24 includes drive electronics and is connected to the transducer 14 through the coaxial cable 16. The control module 24 receives the electrical output impulses from the transducer 14 and detects diminished and lost echo pulses by comparing the output impulse strength values for a given fluid passing through the sensing chamber 20 to a known output impulse strength value for that same type of fluid having no bubbles.

The control module 24 drive electronics include a self contained micro controller (U1) having resident logic that controls timing, logic, sample, compare and user interface functions. The micro controller in the present embodiment is a #PIC16F876-20/SO, 8-bit CmOS, High-performance, RISC CPU microchip and includes all programmable digital logic (resident software). The logic includes an external 20 mHZ clock oscillator (X1) for precise time base control; software based, user programmable boost voltage output level to drive an ultrasonic transducer 14; software based, user programmable trigger pulse frequency output (Sample Rate) to discharge the boost voltage supply to the transducer 14; software based, user programmable signal conditioning for gain or attenuation of signals generated from sample waveforms; software based, user programmable delay logic for controlling the start and width of temporal sampling window gates (manifold 18 Start, manifold 18 Width, bubble Start and bubble Width); software based, user programmable fault threshold levels for data captured during peak detect times; a software based, user programmable filter counter for over-sampling of failed peak detect samples; software derived peak Detect algorithms; and various other software derived conversions, comparisons and logic to communicate results to a user.

The control module 24 also includes an onboard, switching power supply or "boost voltage supply" that generates all of the necessary power and voltage levels the module requires for logic and hardware operation and transducer 14 pulse excitation. The boost voltage supply is used to generate the necessary high voltage impulses needed to excite the ultrasonic transducer 14. The boost voltage supply generates a boost voltage of up to 300VDC. The boost voltage is user programmable from 100–300VDC, in 40 volt increments, and is fed to an energy storage capacitor for use by the pulse driver every time the system pulses the transducer 14. The control module 24 includes monitoring circuits and logic that assures that the boost voltage remains within acceptable limits so as not to damage a transducer 14.

The control module 24 also includes an ultrasonic pulse driver that interfaces between the micro controller and the boost voltage supply and stores energy from the boost voltage supply and discharges it to the ultrasonic transducer 14. The pulse driver includes a digital control logic output, a boost voltage supply output, and a pulse driver. The boost voltage supply feeds energy to a capacitor (C27) where it is stored for later use to excite the ultrasonic transducer 14. The digital control logic generates a 5 microsecond pulse once every 0.20–1 millisecond (user programmable from 1000–5000 Hz repetition rate) to activate the pulse driver. The pulse driver discharges the energy stored in C27 both rapidly (<30 nsec) and fully, creating a crisp impulse to excite the transducer 14.

The control module 24 provides signal isolation, conditioning and waveform conversion used primarily to convert return echo waveforms to digital format for further processing by the micro controller. The signal processing portion of the circuit includes an isolation transformer (T1); an RC network (between T1 and first stage of U18); a signal amplifier (U18); 12-bit High-Speed, a/D converters (U2 & U3); 4.096 Reference Voltage (Q2); software based, user programmable delay logic for controlling the start and width of the temporal sampling window gates (manifold 18 Start, manifold 18 Width, bubble Start and bubble Width); and software based, user programmable signal conditioning for gain or attenuation of signals generated from sample waveforms.

The control circuitry uses multiple, isolated reference grounds and signal processing techniques to help isolate and minimize ambient electrical noise and interference from being passed from one portion of the circuit to another. Analog ground points are shown at 30 in FIG. 14 and are indicated in the other figures by the letter "A" within an inverted triangle symbol. Digital grounds are shown at 32 in FIG. 14 and are indicated in the other figures by an inverted triangle symbol with the subscript "F". Chassis ground points are indicated by the standard chassis ground symbol. The return echoes are passed through an isolation transformer (T1) and are then immediately converted to a DC (peak) voltage through an RC network before being passed on to a dual input, integrated OP-amp (U18, mC33072aD), where user programmable attenuation or gain of the signal may be imposed to bring the amplitude of this peak signal to a level of at or near 4.096 volts DC.

A blanking pulse is used to drive the input of the first stage of the signal amplifier to ground, except when return signals are to be examined. The user programmable detect window start and width times disable this blanking pulse. With the blanking pulse removed, the input to the signal amplifier is free to follow the signal levels coupled to it through the isolation transformer.

The conditioned peak signals are then passed through two a/D converters for later software based comparisons. The a/D converters (maX1241aCSa's) are 12-bit and are referenced to a 1% regulated 4.096 volt DC level supplied by a ZETEX ZR40401F41CT Voltage Reference I/C. Once converted to digital form, the peak signals are compared to adjustable user programmable thresholds to determine if they are of acceptable level, or not.

The assembly 10 also includes an anomaly indicator located in the control panel 12 and connected to the control module 24. The anomaly indicator flags a user in response to a signal from the control module 24 indicating that the assembly 10 has detected a bubble or other anomaly in a fluid stream passing through the fluid channel. The anomaly indicator includes a high intensity red beacon with a 90 dB sonic alarm that can easily be seen and heard by plant personnel. The beacon and sonic alarm are driven by two on-board SPDT relay outputs.

The transducer 14 has a flat front (active) emitter surface 34 that lies flat against a flat manifold outer surface 36 to provide superior acoustic energy pulse coverage throughout the sensing chamber 20. This configuration is superior to a curved surface that focuses the sound beam at a finite distance and obviates the need to machine a matching curvature. The back wall 22 of the sensing chamber 20 is disposed generally parallel to the flat front emitter surface of the transducer 14.

The fluid manifold 18 includes an outer manifold housing 38 constructed of stainless steel. A generally cylindrical acoustic coupling 40 or "plug" is disposed within an end-to-end bore of the housing and is formed from polyphenylene sulfide (PPS). The plug 40 may, alternatively, be formed from any suitable a corrosion resistant, high strength engineered plastic. Polyphenylene sulfide is available from DSM Engineered Plastic Products under the trade name Techtron®. The PPS acoustic coupling provides ultrasonic conduction with good acoustic impedance matching to many fluids, chemical resistance and good pressure/wear performance under use with abrasive adhesives at high pressures. In other embodiments, other suitable high strength plastic materials may be used.

The acoustic coupling includes a notch 42 that defines the sensing chamber 20 and channels the fluid for inspection directly through the sensing field of the transducer 14. To insure total coverage of the inspected fluid, the notch in plug that defines the sensing chamber 20 is only ⅜ inch wide. Because the notch is narrower than the ½ in. diameter transducer 14 ceramic sensing element, the notch forces all fluid to pass well within the sensing field of the transducer 14.

The coupling or plug is also shaped to position the sensing chamber 20 within an optimal sensing range of the transducer 14's sensing field. The optimal sensing range of the transducer 14 depends on the medium it is transmitting through. Through PPS the optimal sensing range is approximately one inch through 1½ inches. The notch is disposed at a distance from the transducer 14 that positions the sensing chamber 20 in the heart of this envelope.

Because the coupling isolates the transducer 14 from the inspected fluid, it protects the transducer 14 from associated pressure effects, erosion from abrasion, temperature effects, and corrosion or chemical attack. Another advantage of the coupling design is that the square shape of the notch in the plug provides a nice flat surface for the transducer 14 to bounce sound off of, improving detection sensitivity.

Because it spaces the transducer 14 from the sensing chamber 20, the coupling also provides a delay period between pulsing the transducer 14 and then listening for echoes. This allows the transducer 14 to "dampen down" or "ring down" after each pulse. In other words, the coupling allows the transducer 14 to stabilize as the sound is propogating through the fluid. It takes 5 or 6 micro seconds for the "ring-down" to occur in the transducer 14. If not given time to ring-down, the ringing (continued sonic transmissions) can interfere with returning echos. The coupling provides approximately 17 micro seconds (8.5 seconds out and 8.5 seconds back) for ring-down to occur.

The acoustic coupling is disposed between the transducer 14 and the back wall 22 of the sensing chamber 20. The acoustic coupling defines a front wall 44 of the sensing chamber 20 parallel to and opposite the back wall 22 and a pair of side walls 46 of the sensing chamber 20 disposed perpendicular to and connecting the front and back walls. The front wall is an interface boundary between the acoustic coupling and the fluid chamber located at the bottom of a notch in the acoustic coupling. The back wall 22 of the sensing chamber 20 is defined by a flat axial inner end surface 46 of an access plug 48. The acoustic coupling and access plug 48 are supported in a coaxially abutting relationship within the cylindrical manifold 18 housing.

The transducer 14 is supported in a coaxially abutting relationship with the acoustic coupling by a generally cylindrical transducer housing 50 that includes a housing cap portion 52 and a removable transducer retaining nut 54 that is supported on an upper end of the cylindrical manifold housing 50.

A wave spring 56 is disposed between the transducer 14 and the transducer retaining nut 54 of the transducer housing 50 and absorbs axial acoustic coupling expansion, deflection or distortion due to pressure or temperature changes. This helps to maintain a proper abutting relationship between the transducer 14 and the acoustic coupling and reduces the possibility of damage from over-tightening of the transducer 14 retaining nut or from an over pressure condition within the fluid manifold 18.

The drive electronics include a window gate comparator. The window gate comparator includes a high side comparator that includes a peak detect amplifier configured to detect absolute peak amplitudes occurring within the echo waveforms.

The drive electronics includes electronics and software configured to modify echo signals that require either additional gain or attenuation to place their amplitudes within a proper operating range of the window gate comparator.

Digital control logic is included in the drive electronics and examines at least two discrete return echo amplitude periods during each-pulse-echo cycle and controls two independently adjustable temporal sampling window gates or scanning temporal envelopes for sampling echoes or returned pulses. One of the adjustable temporal sampling window gates is a manifold 18 window gate that provides sonic communication between the transducer 14 and the front wall of the fluid chamber and detects echoes that reflect from the front wall. This manifold 18 echo is virtually unaffected by process fluids within the fluid chamber and thus provides a known reference that the electronics are operating and that the transducer 14 is pulsing and receiving echoes at regular intervals with repeatable amplitudes. If the returned value from the manifold 18 window exceeds the manifold 18 alarm threshold, then a "system OK" alarm output is turned on and will remain on until the system is no longer "OK", or until a physical problem arises within the controller's electronics.

The other of the adjustable temporal sampling window gates is a bubble window gate that provides sonic communication between the transducer 14 and the back wall 22 of the fluid chamber and detects echoes that reflect from the back wall 22 of the fluid chamber. The manifold 18 window gate and bubble window gate have independently digitally programmable and adjustable start and width times. The control module 24 is designed and programmed to detect the presence of bubbles by detecting diminished back wall echo amplitudes.

The digital control logic provides an adjustable scanning pulse repetition rate of between 1000 and 5000 pulses per second. The pulse-echo intervals (or sample frequencies) are user adjustable.

The digital control logic employs temporal filtering of output signals from the window gate comparator to select only a return echo period of interest and to strip out extraneous echo signals.

The digital control logic causes the transducer 14 to send out a pulse then examines the amplitude of the returned echo of the pulse and compares the amplitude of the returned echo against an adjustable threshold value to determine, in each cycle, whether or not the echo amplitude indicates the presence of a bubble or other anomaly. If a returned waveform echo passes this test, then an internal value of the filter counter is reset to zero and the bubble alarm output is not turned on. If the returned waveform echo does not pass this test, then a fault bit is set and passed, through internal logic, to the anomaly detecting assembly 10's filter counter.

The comparator threshold of the assembly 10 is adjustable to allow an operator to set a bubble size threshold that must be exceeded before the assembly 10 will output a fault signal.

Figure 14:
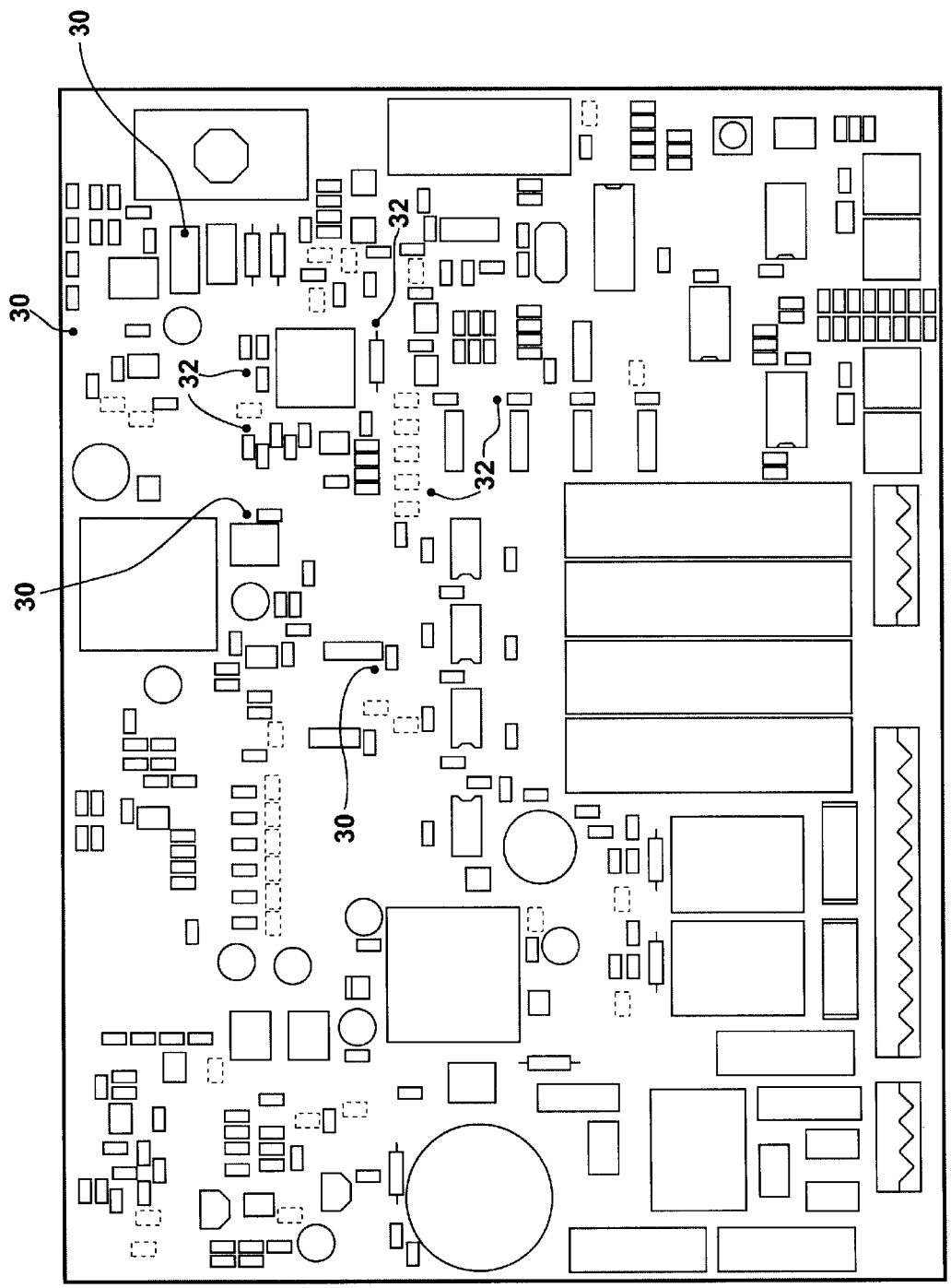
FIG. 14 is a plan view of an electronics module circuit board of a control module of the control panel assembly of FIG. 10.
Figure 15:
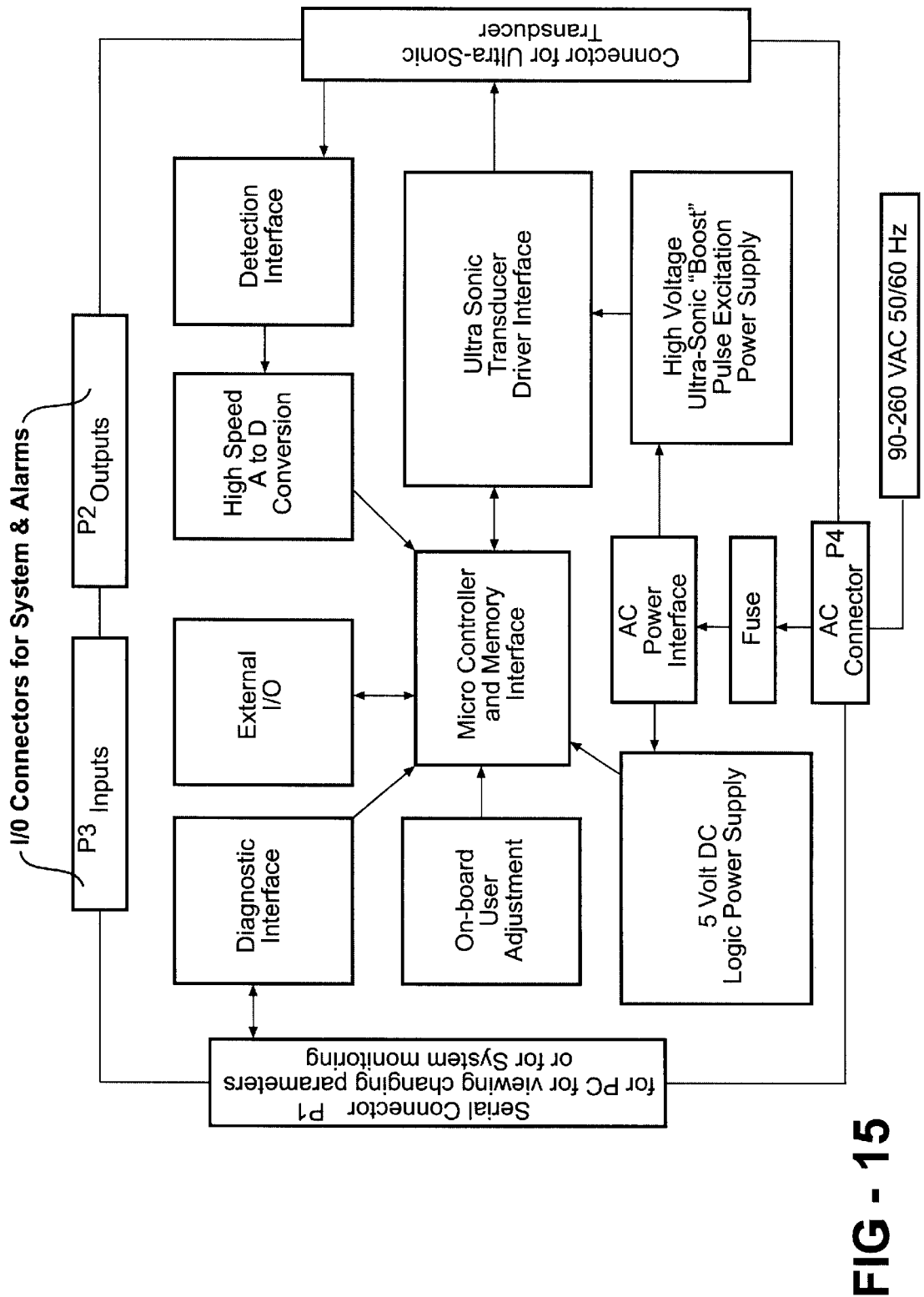
FIG. 15 is a block diagram of the electronics module circuit board of FIG. 14.
Figure 16:
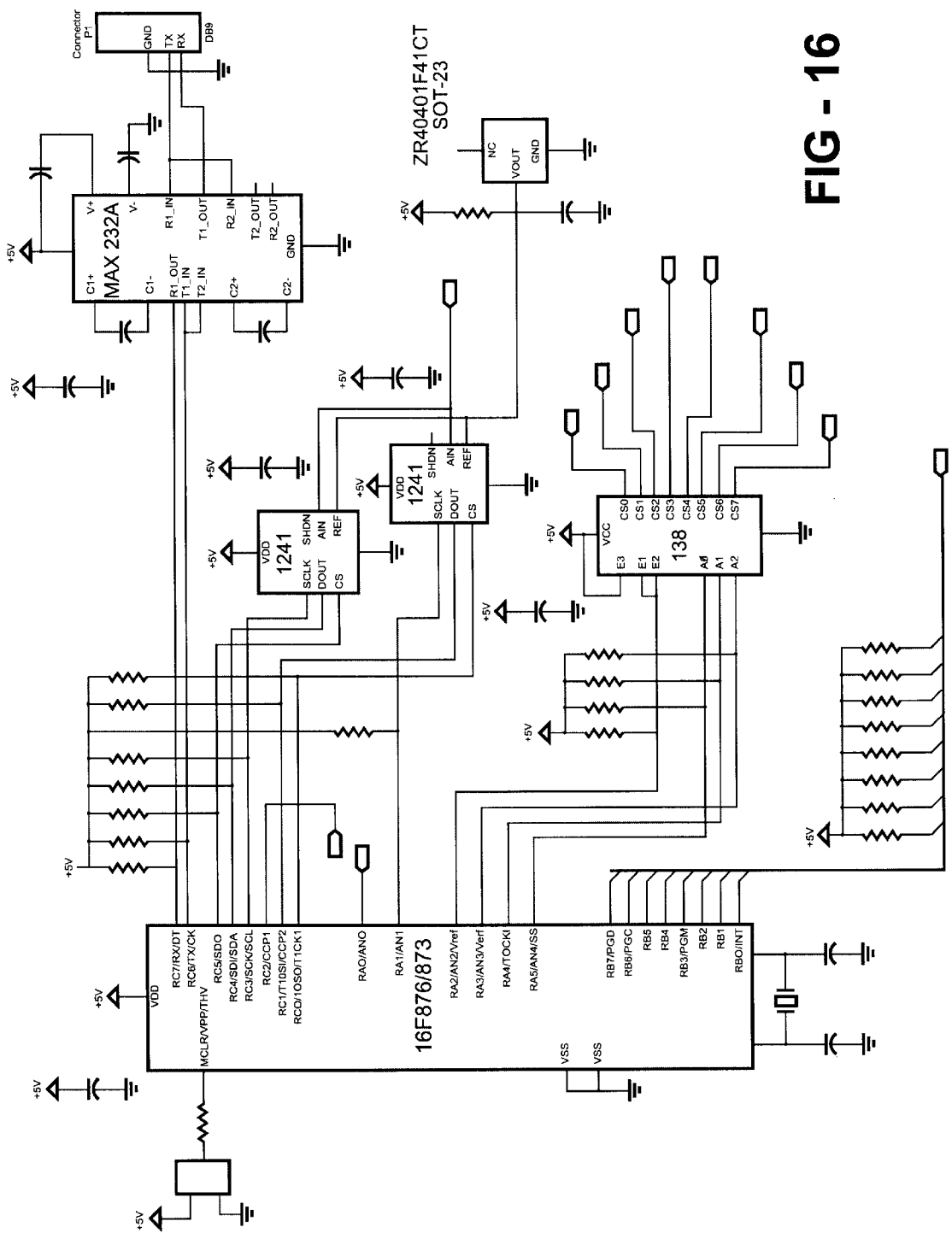
FIG. 16 is an electrical schematic of a main controller and analog to digital conversion elements of the electronics module circuit board of FIG. 14.
Figure 17:
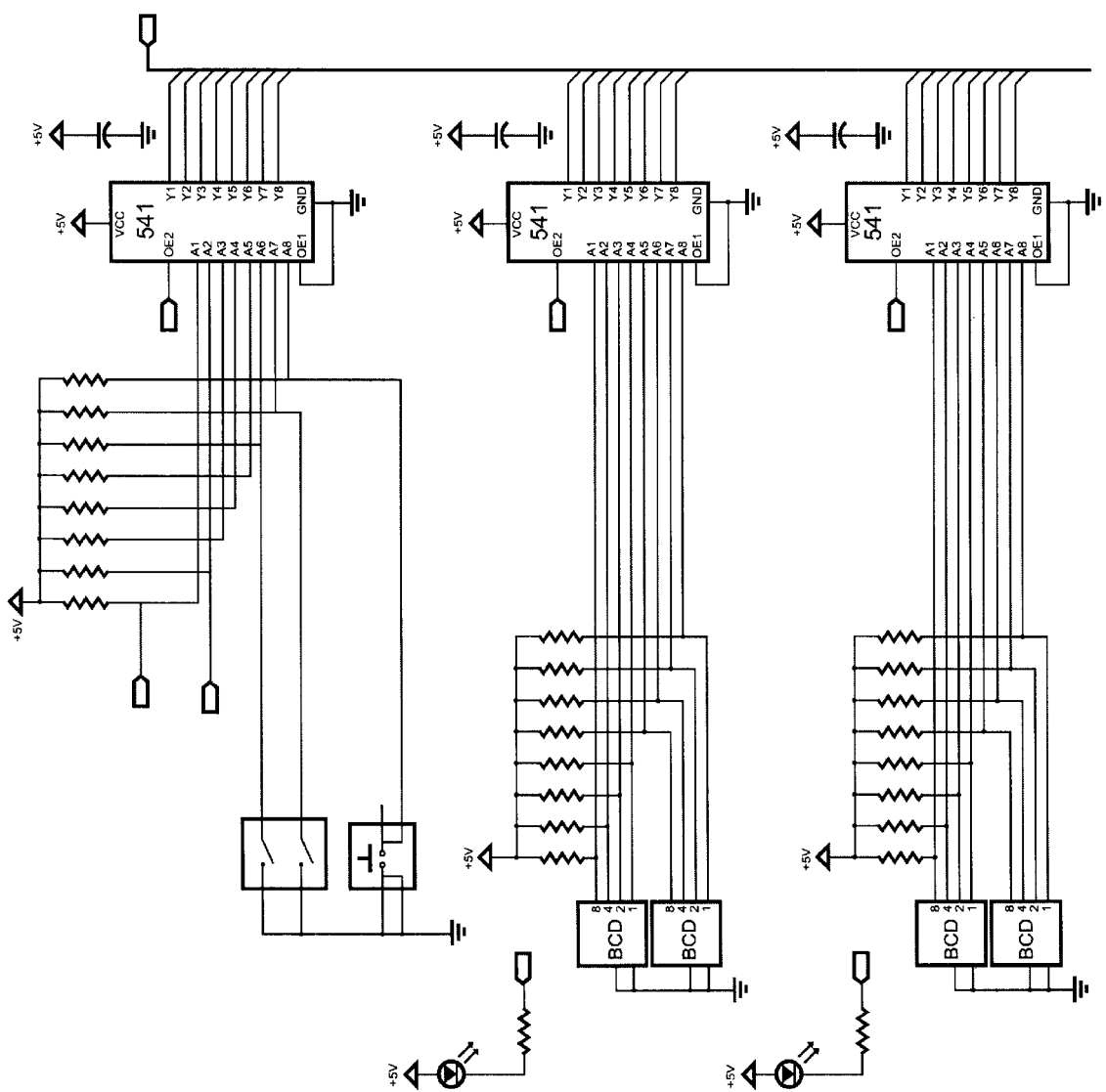
FIG. 17 is an electrical schematic of a logic I/O interface of the electronics module circuit board of FIG. 14.
Figure 18:
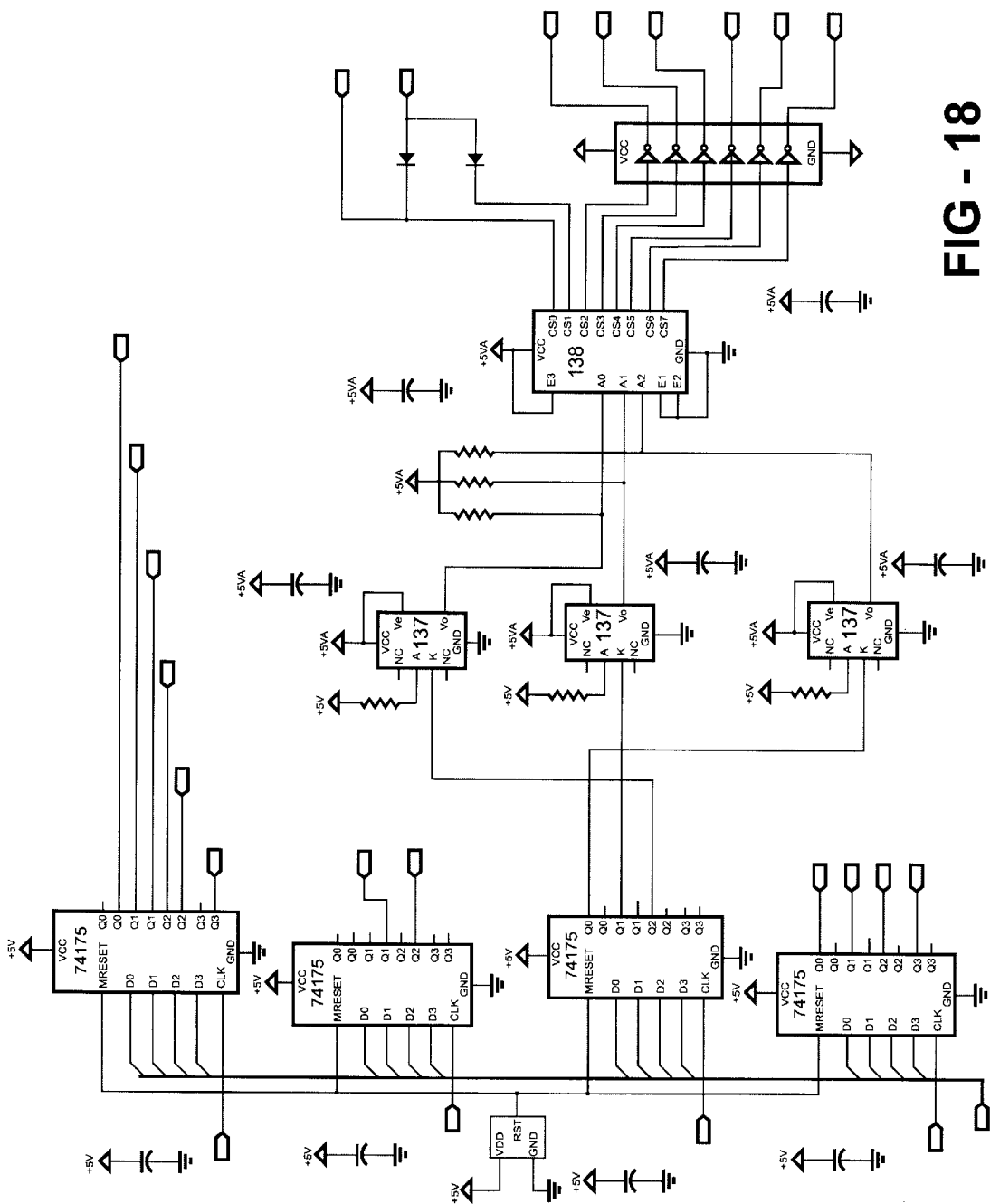
FIG. 18 is an electrical schematic of on board output drivers of the electronics module circuit board of FIG. 14.
Figure 19:
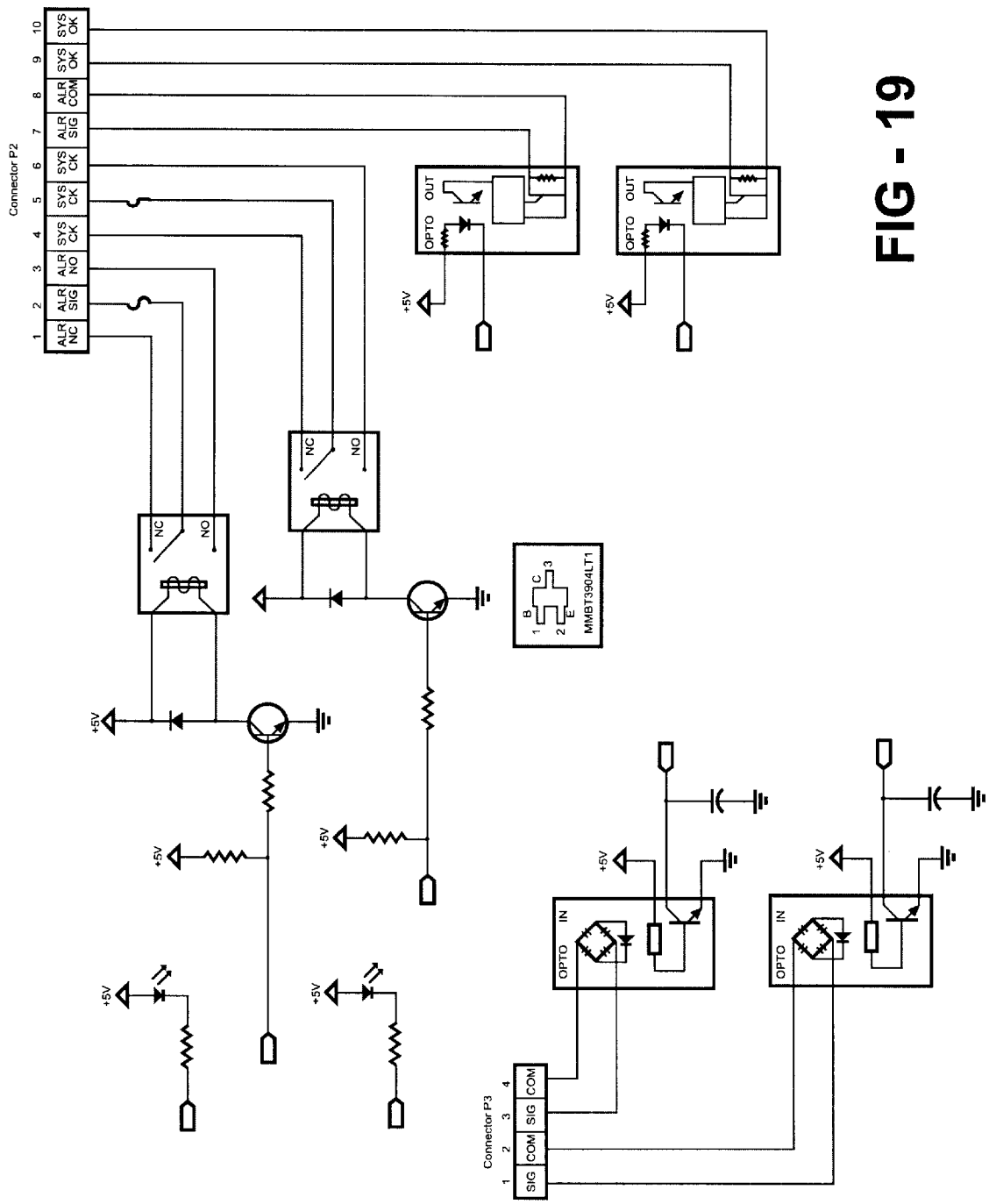
FIG. 19 is an electrical schematic of a relay and isolated outputs of the electronics module circuit board of FIG. 14.
Figure 20:
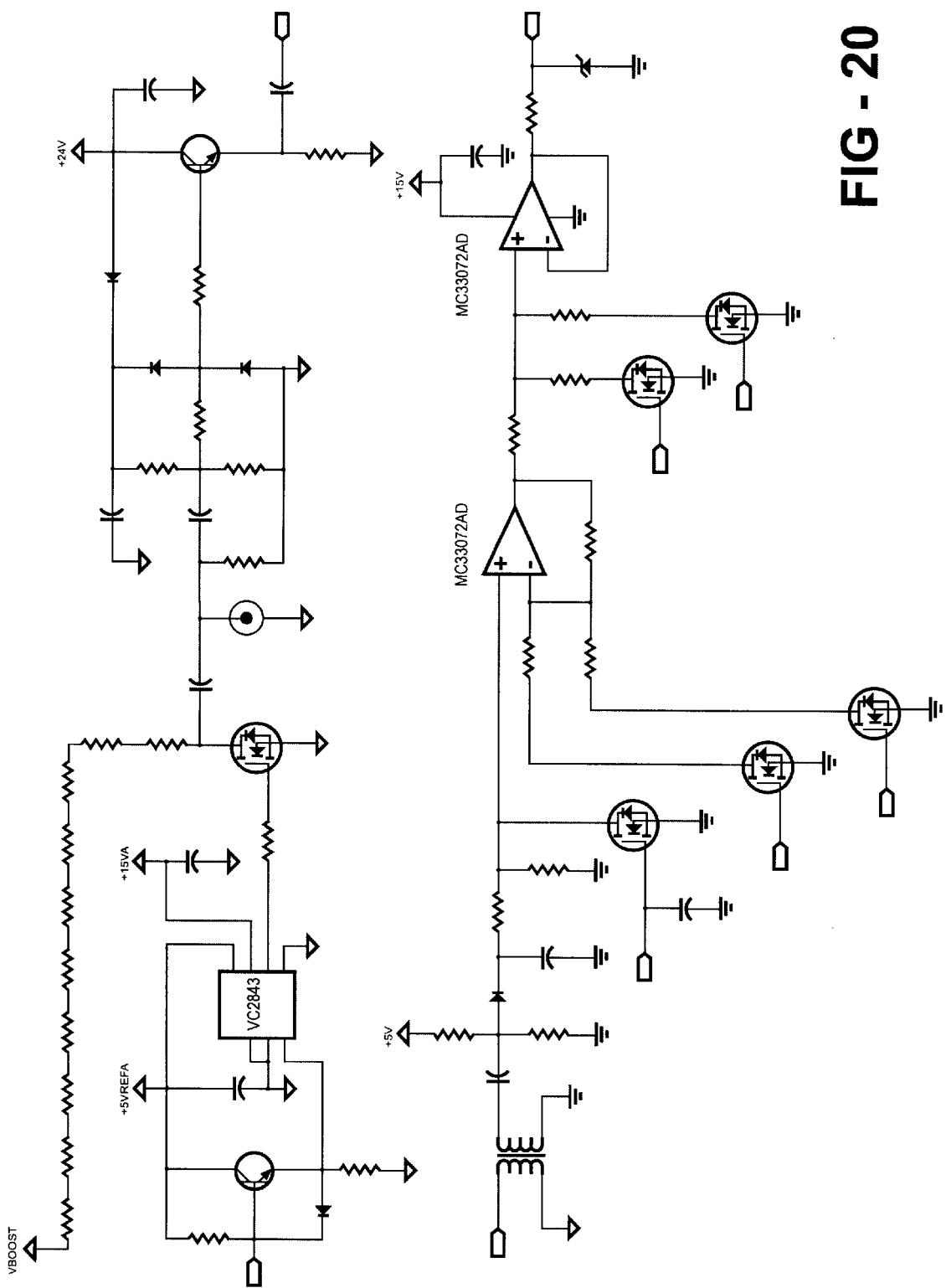
FIG. 20 is an electrical schematic of a pulse signal drive and read conditioning of the electronics module circuit board of FIG. 14.
Figure 21:
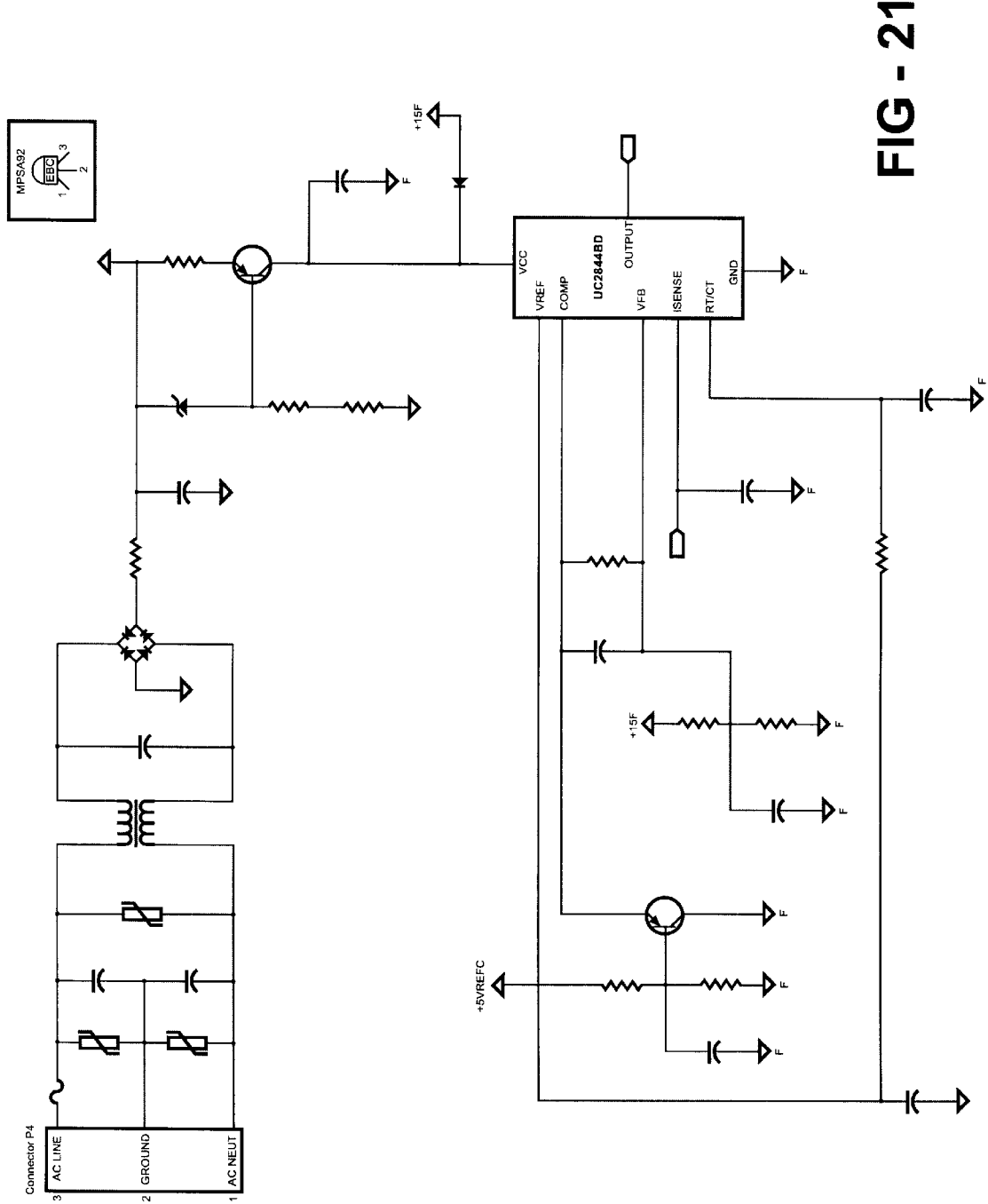
FIG. 21 is an electrical schematic of a power supply AC line interface of the electronics module circuit board of FIG. 14.
Figure 22:
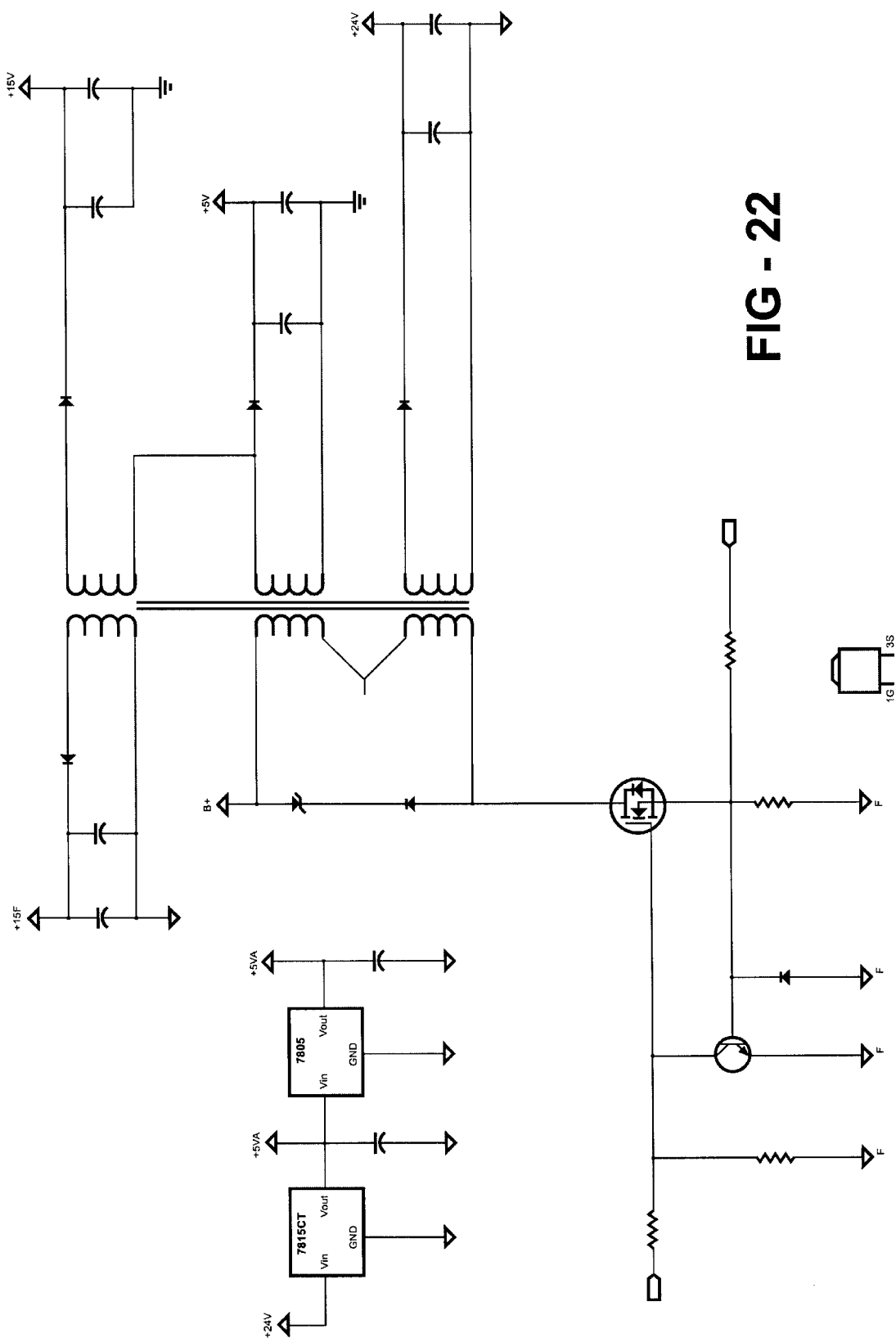
FIG. 22 is an electrical schematic of power supply rails of the electronics module circuit board of FIG. 14.
Figure 23:
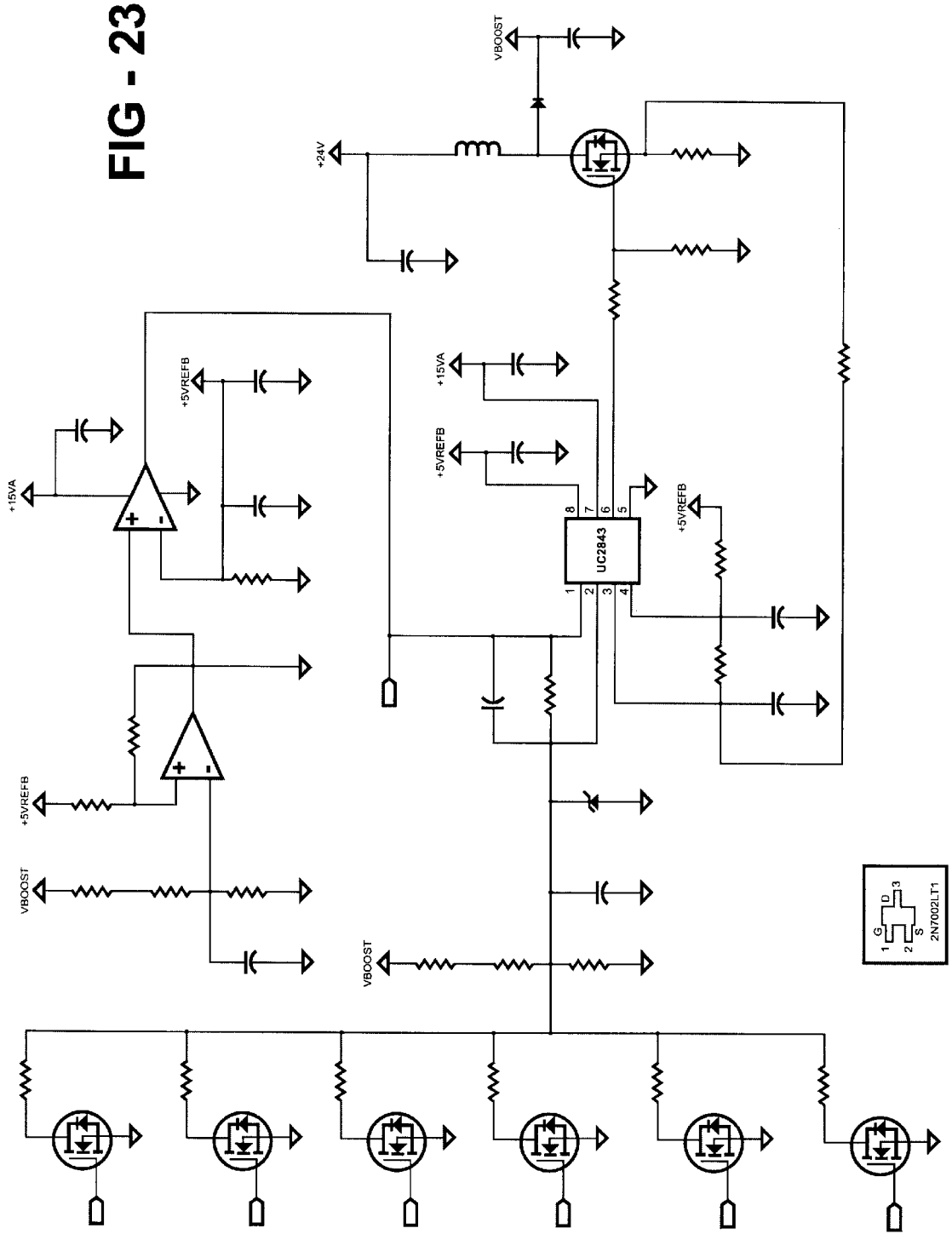
FIG. 23 is an electrical schematic of boost supply of the electronics module circuit board of FIG. 14.

Two board mounted BCD switches are used to adjust the sensitivity of the assembly 10 as shown at SW2 and SW3 in FIG. 14. The switches are used together as a value of 00–99 with increasing numbers representing increased sensitivity (higher sensitivity numbers will cause the assembly 10 to trigger on smaller bubbles). Eventually, if the sensitivity is set too high, the assembly 10 will exhibit a continuous "bubble" alarm, even when no such condition exists. The opposite can also be true. If the sensitivity is too low, the assembly 10 will not respond to any bubbles. The optimal sensitivity setting is an empirical value that must be determined by the user to suit each particular application. The factory default setting of these switches is 50.

The digital control logic includes a filter counter and is programmed to turn on the anomaly indicator bubble alarm when the number of failed pulse-echo cycles equals a preset threshold value of the filter counter. The threshold value of the filter counter is user adjustable. Two board-mounted BCD switches shown at SW4 and SW5 in FIG. 14 are used to adjust the filter counter such that 1+"n" number of continuous samples must show the presence of bubbles or other anomalies before the control module 24 will activate an alarm. The factory default value of these switches is 01 and most installations will operate well at this or any setting between 0 and 10. Lower settings will allow the assembly 10 to pick up finer bubbles and higher settings will require larger bubbles to produce a bubble alarm output.

There are two anomaly fault monitoring modes. The selector for either mode is switch SW1-1 which is shown on the bottom right of the circuit board in FIG. 14. The switch has two positions, zero (0) and one (1). Moving switch SW1-1 to the zero position selects a "Fault on Enable Monitor" mode of fault monitoring. Moving switch SW1-1 to the 1 position selects a "Fault on Continuous Monitor" mode for fault monitoring.

In the Fault on Continuous Monitor mode the anomaly detecting assembly 10 continuously monitors the fluid manifold 18 for discrepancies in the pulse-echo cycles. Alarms will be activated immediately if conditions are not normal.

The Fault on Enable Monitor mode is similar to the Fault on Continuous Monitor mode, but the anomaly detecting assembly 10 will only turn on the bubble alarms if an "Enable" input is sensed. Fault on Enable Monitor mode may be used to help increase sensitivity while limiting susceptibility to false triggers at idle. False triggers at idle may be generated by physical variations, such as viscosity, of the fluid being monitored. The anomaly detecting assembly 10 still functions as described above except that, if it is not enabled, the bubble alarm output will not be turned on when conditions are abnormal. The anomaly detecting assemblies are set in the Fault on Enable Monitor mode at the factory.

The control module 24 includes a user electrical I/O interface that accepts input signals from and provides output signals to a user-provided external controller such as an industrial controller or PLC configured to receive the output signals from the digital control logic and to output signals representing information relating to the number of bubbles detected. The I/O interface includes 2 user inputs, either OPTO-22 120VaC (Standard) or 24VDC (Optional). Input #1 (Opto 3) is an enable (run) and input #2 (Opto 4) is an alarm reset. The I/O interface includes two user outputs, either OPTO-22 120VaC (Standard) or 24VDC (Optional). Relay output #1 (and OPTO #1), are for "Bubble Detected"; This output is logic 0 (off) when the anomaly detecting assembly 10 is functional and no bubbles are detected. Relay output #2 (and OPTO #2), are for "System OK". This output is logic 0 (off), held at logic 1 (on) when the anomaly detecting assembly 10 is active and is receiving signals at a regular and normal frequency. The I/O interface also includes a single serial interface port (DB9-Pin, male) for connection of a user supplied PC.

The transducer 14 is a semi-custom version of a generic 2.25 MHz, 0.50 inch diameter industrial immersion transducer 14 available from Krautkramer company of Lewistown, Pa., that includes standard ceramic elements, standard design and assembly techniques and having a housing modified to be as physically small as possible and to accommodate the wave spring. The housing is also modified to be held in place by a finger-tightened nut to allow fast, easy and firm attachment of the transducer 14 to the manifold 18. The pigtail electrical connector is also modified by moving the electrical connection away from the main body to reduce size and ease mounting.

The transducer 14 converts the output pulse from the pulse driver into ultrasonic acoustic energy that propagates through a plastic Techtron acoustic coupling 40 and into the fluid chamber 20. Eventually, this acoustic energy encounters discontinuities such as the interface between the Techtron acoustic coupling and the fluid medium, and the fluid medium and the back wall 22. Every discontinuity encountered results in a return echo being generated. These echoes are reflected back to the transducer 14 which, upon receiving them, converts the energy back into electrical impulses to be processed by the electronics.

The control module 24 includes a user serial interface that connects the module to a user provided computer such as a PC to allow stored parameters and diagnostics of system operation to be viewed and adjusted.

The control module 24 includes a self contained micro controller having resident logic configured to control timing, logic, sample, compare and user interface functions. An onboard switching power supply generates power and voltage levels that the control module 24 requires for logic and hardware operation. The onboard switching power supply also generates a boost voltage supply for transducer 14 pulse excitation to generate the necessary high voltage impulses needed to excite the ultrasonic transducer 14. An ultrasonic pulse driver interfaces between the micro controller and the boost voltage supply and stores and discharges energy created in a boost voltage section of the module to the transducer 14. The control module 24 also includes circuit elements that isolate and condition signals and convert waveforms (primarily return echo waveforms) to digital format for further processing by the micro controller.

In practice, detecting gas bubbles in a high-pressure sealant stream can be accomplished by providing the sensing chamber 20 in a fluid channel, providing the ultrasonic transducer 14, associated drive electronics anomaly indicator, connecting the ultrasonic transducer 14 and associated drive electronics to the sensing chamber 20 and connecting the anomaly indicator to the drive electronics. The industrial immersion transducer 14 is then modified as described above.

In a fluid dispensing application, the fluid manifold 18 is then mounted as close to a point of fluid discharge as possible for best performance and in line with a fluid passage to be monitored. If the fluid dispensing application includes a fluid applicator gun, the fluid manifold 18 is preferably mounted just ahead of a valve or nozzle of a fluid applicator gun.

Since air, by it's nature, is highly compressible, the bubbles that pass through the fluid manifold 18 may be much smaller than they would appear in a finished product (usually at ambient air pressure). Because the nominal bubble size is dependent on the surrounding pressure, it is very important to place the U.S.B.D. fluid manifold 18 at the lowest system pressure point (usually at or very near the point of application) to achieve the best possible resolution. Another reason for placing the fluid manifold 18 close to the point of application is for more practical reasons. When the system detects bubbles, the bubbles will appear at the nozzle sooner if the sensor is located just up-stream from the nozzle. This will help to track down where the bubbles "went" after being flagged when they went through the fluid manifold 18 and will help to determine on which job bubble-contaminated adhesive was used.

After mounting the fluid manifold 18, a fluid to be inspected is then passed through the sensing chamber 20 and the drive electronics are actuated to operate the transducer 14 and detect bubbles in the fluid. The drive electronics are preprogrammed to cause the transducer 14 to repeatedly bounce ultrasonic impulses off the back wall 22 of the sensing chamber 20 at regular intervals, and to then monitor the returned echoes from within the sensing chamber 20 during each pulse-echo cycle looking for anomalous waveform echoes that indicate the presence of bubbles. The lengths of the intervals between impulses (the sampling rate) is then adjusted to optimize bubble detection sensitivity to the flow requirements of the fluid system being monitored.

Setting the sensitivity of the anomaly detecting assembly 10 involves some trial and error, and, when beginning the process it's best to err on the "too sensitive" side. For optimal performance the anomaly detecting assembly 10 should be tuned to a given application while fluid is moving through the sensing manifold 18. Therefore, it's important to set the sensitivity while dispensing (or purging) material continuously as follows:

1 First, the ALARM SW1-1 Fault Monitor Mode switch is set to 1.
2 The anomaly detecting assembly 10's Filter BCD switches are set to 0,1 (one unit).
3 The anomaly detecting assembly 10's 'unit' sensitivity adjustment (right) BCD switch is set to nine.
4 Then, the sensitivity BCD setting is increased by tens (using the left rotary switch shown at SW2 in FIG. 14) incrementally until a continuous bubble alarm is encountered.
5 The sensitivity is then decreased by ones (using the right rotary switch) until the bubble alarm goes off and remains off.
6 A note is made of the value of the sensitivity BCDs at this point. This value is the maximum level of sensitivity that may be used for this application, though it may not be a practical level to use because the anomaly detecting assembly 10, at this setting, is very close to becoming unstable. Normally, for an installation at, for example, a Urethane Glass Cell, this value should occur at BCD values above 75.
7 For many applications, usable sensitivity values will be 20, or more, counts below this maximum level of sensitivity. As such the user should start with a sensitivity setting that is 20–25 counts below the maximum level. This value of sensitivity can always be adjusted later if it proves unsatisfactory.

After setting the system sensitivity as outlined above, the performance of the anomaly detecting assembly 10 is monitored over a period of a few days (or weeks). After this extended period of monitoring it may be necessary to make further adjustments to the sensitivity setting. To do this, the sensitivity settings are incrementally increased or decreased to suit the particular application. Please note that while any change in sensitivity is effected immediately, it will not be noticed until the next occurrence of air bubbles is encountered. For this reason minimal adjustments should be made and one should wait to see the results before making further adjustments.

The anomaly detecting assembly 10 should be set for the highest level of sensitivity that does not generate nuisance alarms. Often this sensitivity level will be, approximately 20 to 25 units below the maximum level of sensitivity. When operated at elevated sensitivity levels, e.g., within 5 to 15 units of the maximum level of sensitivity, process fluid variances become increasingly important and may cause adverse reactions on the anomaly detecting assembly 10. This is not to say that the anomaly detecting assembly 10 cannot be used reliably at elevated sensitivity levels, only that it must be used in the "Fault on Enable Monitor" mode. Also, if the fluid system has been idle for an extended period of time, to reestablish nominal fluid characteristics a small amount of material may have to be purged before production. For most production equipment, where the fluid system is being used on a regular basis, the anomaly detecting assembly 10 can probably be used at elevated sensitivity settings with reliable results.

The drive electronics are preprogrammed to examine at least two discrete return echo amplitude periods during each pulse-echo cycle. To assure that the system is functioning normally, and that no bubbles are detected, the first return echo amplitude period verifies that the transducer 14 is sending and receiving echoes by providing sonic communication with the interface between the acoustic coupling and the fluid chamber. During each pulse-echo cycle, returned waveform echoes are monitored and compared, through internal logic, to a preset manifold 18 alarm threshold value to determine if sound waves are, in fact, making their way to the detection chamber. This preset threshold is a user adjustable feature designed to optimize the fault capturing method to the user's specific needs.

The second return echo amplitude period provides sonic communication with the back wall 22 of the sensing chamber 20 such that the drive electronics are able to detect bubbles in the sensing chamber 20 by detecting diminished back wall echo amplitudes. Return echo waveform amplitude is a direct indication of the uniformity of a liquid that is flowing through an imaging chamber during a scanning pulse. A system may therefore be calibrated against known return echoes generated by various fluids that contain no bubbles. Any bubbles that pass through the sensing manifold 18 will absorb and reflect some of the acoustic energy that would normally strike the back wall 22. The return echoes will then have a lesser amplitude than when the fluid manifold 18 contains no bubbles. By sensing this amplitude variation, and comparing it to a preset threshold, it is relatively easy to detect the difference between normal fluid flow and a bubble.

The anomaly detecting assembly 10 includes an interface software application that allows a user to communicate with the control module 24, adjust settings and monitor various aspects of system operation. The application, entitled Jesco.exe is a Microsoft Windows® executable application program and is compatible with Microsoft's Windows 9x®, ME®, NT® and 2000® operating systems.

The status of the transducer 14 and the coaxial cable 16 connecting the transducer 14 to the control module 24 are monitored for open or short circuit conditions and such conditions are subsequently indicated to an operator and/or supervisory controller. Adequacy of the acoustic coupling is verified by programming the drive electronics to provide a temporal sampling window gate that provides sonic communication between the transducer 14 and an interface boundary between the acoustic coupling and the fluid chamber and detects echoes that reflect from that interface boundary. Internal checks are also performed to verify that the pulse driver voltage is at a specified level and, if not, the assembly 10 is shut down to avoid damaging the transducer 14 with excessive voltage/power. A "System OK" indicator output is also turned off as a result.

The bubble detection assembly 10 includes an interface software application that allows a user to communicate with the control module 24, adjust settings and monitor various aspects of system operation. The application, entitled Jesco.exe is a Microsoft Windows® executable application program and is compatible with Microsoft's Windows 9x®, ME®, NT® and 2000® operating systems.

The application is loaded onto a PC running one of the above operating systems and having at least one open serial communications port. A 9-pin female×9-pin female serial interface cable is used to connect the PC to the control module 24 of the bubble detector assembly 10.

Figure 24:
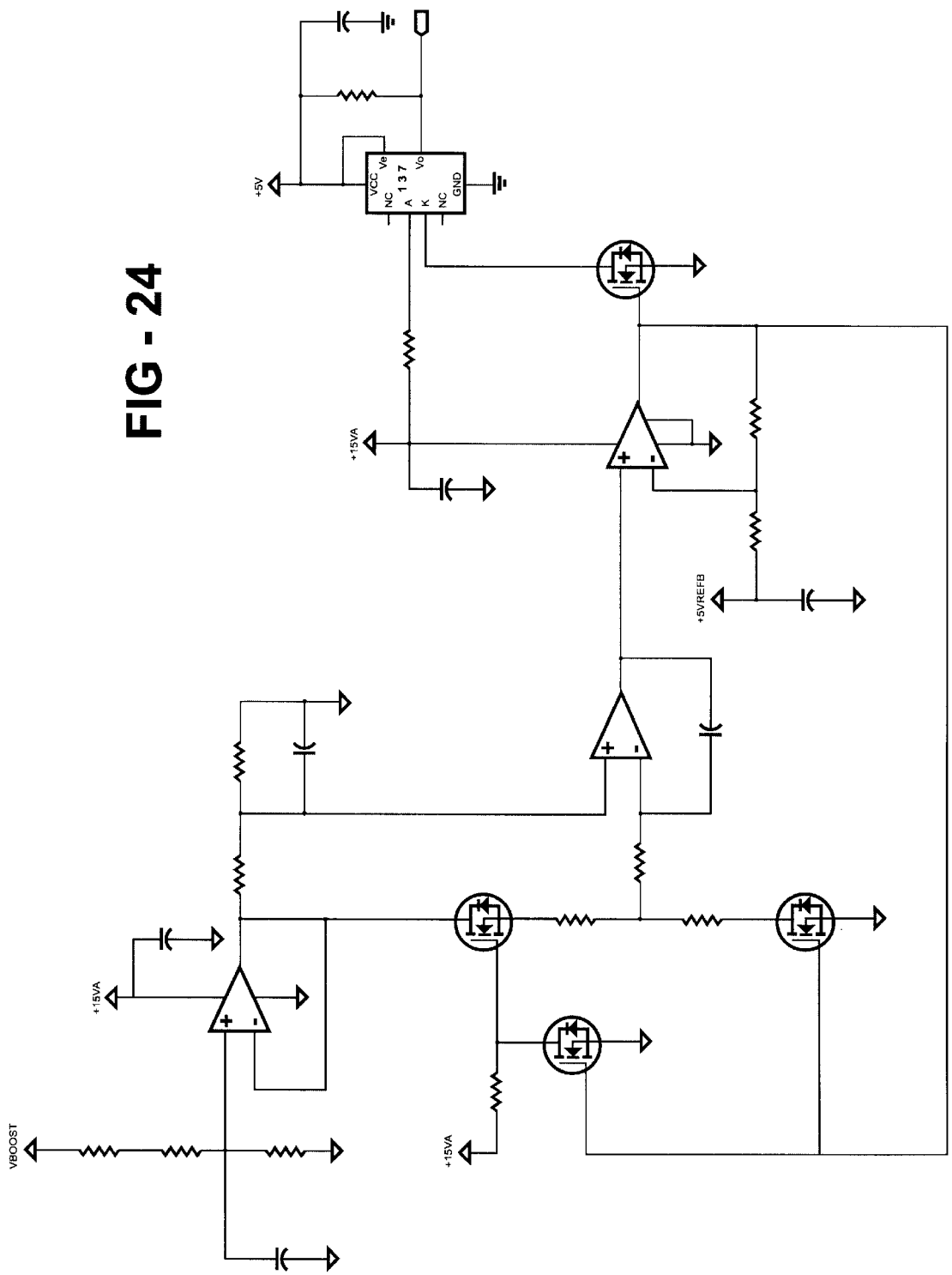
FIG. 24 is an electrical schematic of a boost monitor of the electronics module circuit board of FIG. 14.
Figure 25:
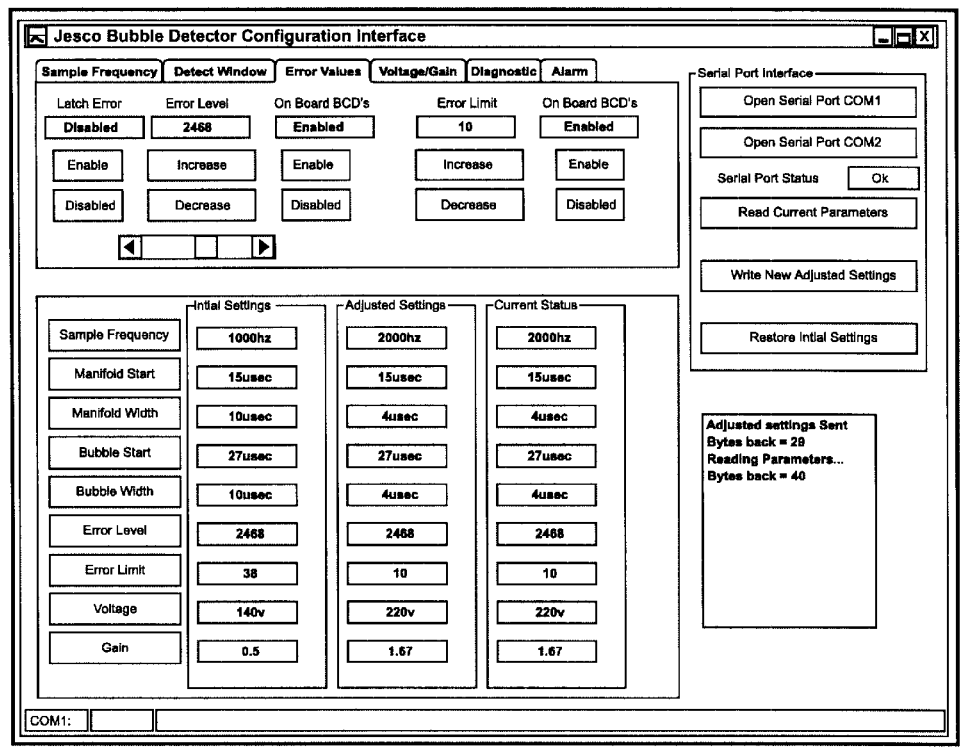
FIG. 25 is a screen shot of bubble detector interface software for controlling the bubble detection assembly of FIG. 1 with an error values selected for display.
Figure 26:
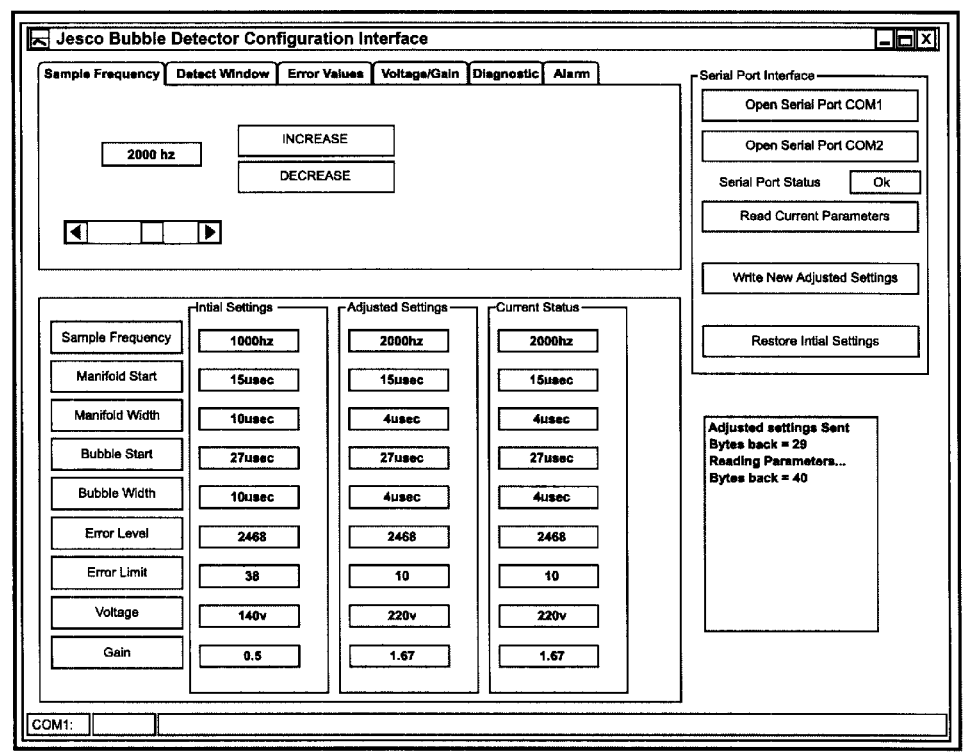
FIG. 26 is a screen shot of the bubble detector interface software of FIG. 24 with sample frequency selected for display.

The application is launched and power is applied to the control module 24 by closing a circuit breaker on the control panel 12. A communications port is then opened by selecting the appropriate button (COM1 or COM2) in the upper right-hand portion of a configuration interface screen shown in FIGS. 24–26 and 28–30. The "Read Current Parameters" radio button, located midway down on the right-hand side of the interface screen, is then pressed. At this point the screen should resemble the screen shown in FIG. 24.

The screen shown in FIGS. 24–26 and 28–30 is divided into three primary sections. Beginning at the top left are tabs for various sub menus to allow a user to gain access to settings and/or modify stored parameters. In the top right portion of the screen is the communications area and in the lower left portion are parameter columns listing stored parameters for the system.

Various settings may be adjusted by selecting the appropriate tab or radio button from the interface screen. A user can gain access to the sub menus by selecting the associated tabs at the top of the screen and can select parameters for adjustment by pressing the appropriate radio button to the left of the parameter columns. Each tab or radio button contains specific adjustments or displays to a single value or group of values pertaining to that function.

After making any changes to the system parameters the settings are transferred to the control module 24 by pressing the "Write New Adjusted Settings" radio button located below the "Read Current Parameters" button on the right side of the interface screen.

The next step in setting up the system is to press the Sample Frequency Radio Button, or to select the Sample Frequency tab. Your screen should then resemble the screen shown in FIG. 25.

Adjusting the Sample Frequency value adjusts the number of pulse-echo cycles (or sample rate) of the anomaly detecting assembly 10. Adjustments may be made to increase or decrease the sample frequency, but care must be taken not to use too high of a Sample Frequency along with too high of a Pulser Voltage setting since the power output of the system (nominal watts) is defined by the product of these two settings, and a power level that could damage the transducer 14 could result.

The sample frequency should be set high enough to take at least 10 samples of the fluid stream as it passes through the sensing manifold 18. The number of samples that will be taken on a given fluid stream is determined as follows:

n=Sample Frequency (measured in samples per second)

Q=Material Flow rate (measured in cubic inches per second)

v=Material velocity through the sensing manifold 18 (measured in inches per second)

A=cross-sectional area of the fluid passage (for a standard manifold 18 this is 140625 in$^2$.)

v=Q/A d=sensed distance of the fluid manifold 18 (for a standard manifold 18 this is 0.280 in.)

t=the time it takes, in seconds, for fluid to traverse a sensed distance (d) of the fluid manifold 18.

t=d/v

To gather at least 10 samples of a fluid stream, the sample rate (frequency) should be set to:

n=1/[(t)/(10 samples)]

For most installations, a sample frequency of 1000–2000 Hz proves more than sufficient to monitor the process fluid effectively at fluid flow rates of up to one gallon per minute (1 GPM) while providing roughly 14–28 samples of the fluid passing through the fluid manifold 18. Unless the fluid system operates at flow rates in excess of 2 GPM, increasing the frequency will not generally increase the performance or sensitivity of the system to air bubbles. For practical reasons the system should be operated at the lowest sample frequency that proves effective to capture bubbles of interest.

To adjust window widths, the Manifold Start, Manifold Width, bubble Start or bubble Width Radio Button, or the Detect Window tab is selected. The screen should then resemble the screen shown in FIG. 26.

The detect window settings are used to center the sample periods of each Pulse Echo cycle at the appropriate waveforms. Adjusting these settings requires the use of an Oscilloscope. Each cycle of the anomaly detector assembly 10 includes a pulse of electrical energy from the control module 24 to the transducer 14 where it is converted to acoustic energy (an ultrasonic sound wave). As the sound wave travels outward, away from the front face of the transducer 14, it encounters discontinuities such as the interface between the front face of the manifold 18 (Bottom of the milled notch in the Acoustic Coupling 40) and the fluid within the sensing chamber 20. Each discontinuity will result in an echo being generated. The control module 24 examines these echoes at the times specified by the Detect Window settings. These echoes may occur at different times for different applications, and/or with different materials being monitored and exactly when they will occur is determined primarily by the velocity of sound through that particular medium and the distance that the sound must travel to traverse that medium.

The Window Start periods with respect to $t_0$ (where $t_0$=Pulse initiation) are placed approximately 2 μsec (microseconds) before the first full positive peak in that echo waveform as displayed on an Oscilloscope. The window widths should be set wide enough to cover the first three full positive peaks (usually around 4 μsec). Wider settings will not generally harm anything, so long as the value of Manifold Start+Manifold Width does not equal or exceed the bubble start time.

Adjustment ranges for the detect windows are as follows:

Manifold 18 Start; Range 7<Set Point <400 μsec in 2 μsec increments. Manifold Start time defines the beginning of the window opening for monitoring the Manifold Start (Front Wall) echo of the fluid manifold 18.

Manifold 18 Width; Range 2<Set Point <40 μsec in 2 μsec increments. Manifold Width time defines the window open time for monitoring the Manifold Start (Front Wall) echo of the fluid manifold 18.

Bubble Start; Range 7<Set Point <400 μsec. bubble Start time defines the beginning of the window opening for monitoring the bubble (Back Wall) echo of the fluid manifold 18.

Bubble Width; Range 2<Set Point <40 μsec in 2 μsec increments. bubble Width time defines the window open time for monitoring the bubble (Back Wall) echo of the fluid manifold 18.

Figure 27:
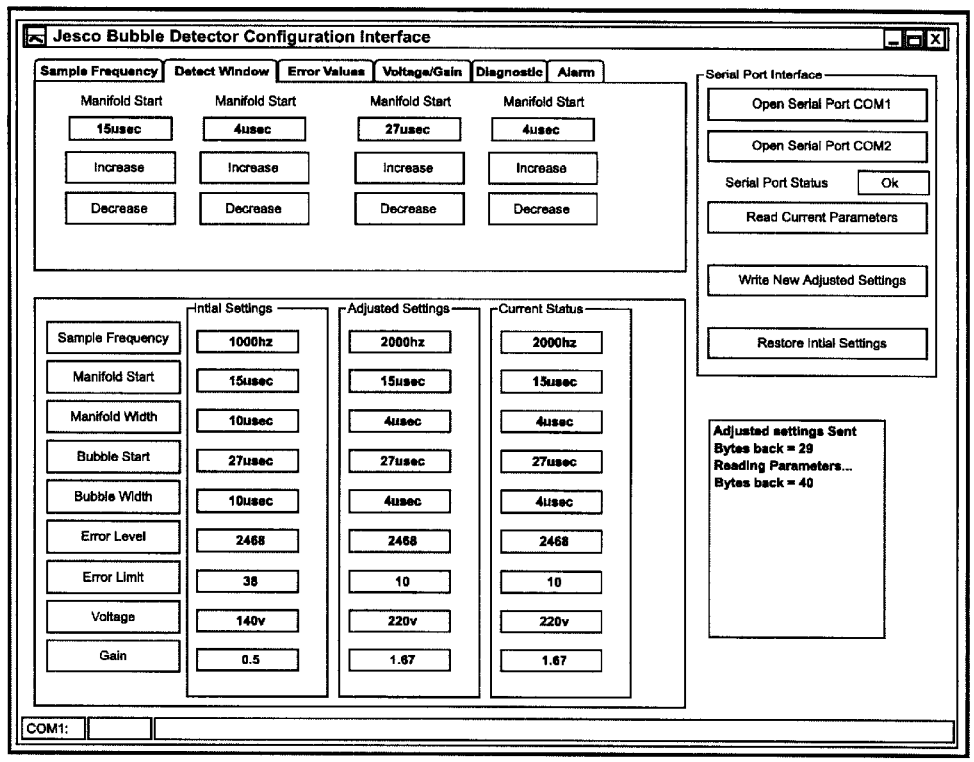
FIG. 27 is a screen shot of the bubble detector interface software of FIG. 24 with detect window parameters selected for display.
Figure 28:
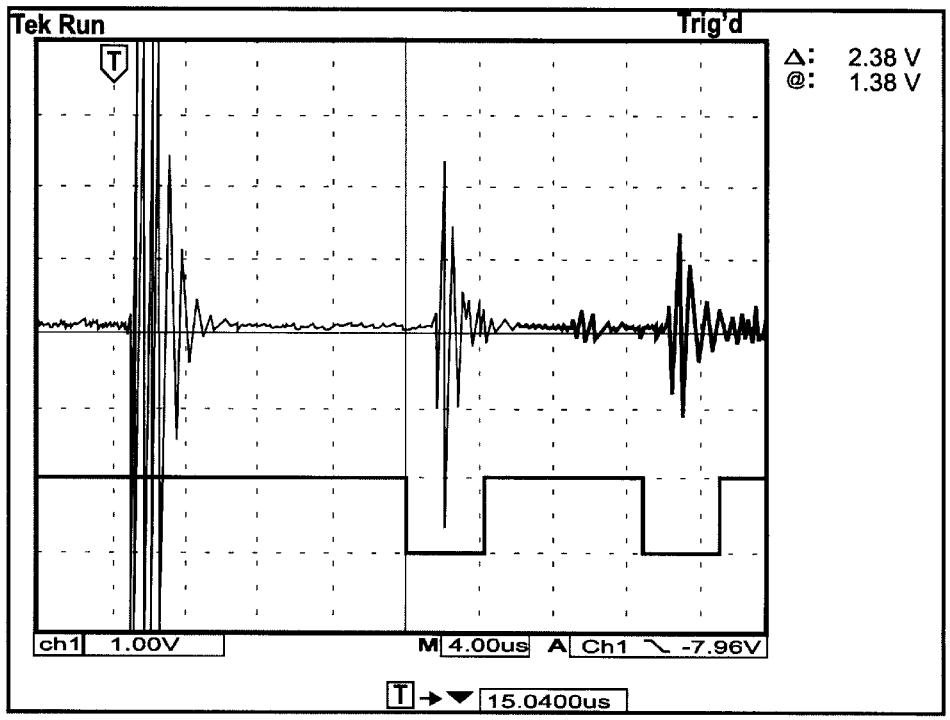
FIG. 28 is an oscilloscope trace of an oscilloscope connected to the control module of FIG. 14 and showing transducer echo and window periods of a typical echo waveform and blanking pulse response experienced during adjustment of window settings.
Figure 29:
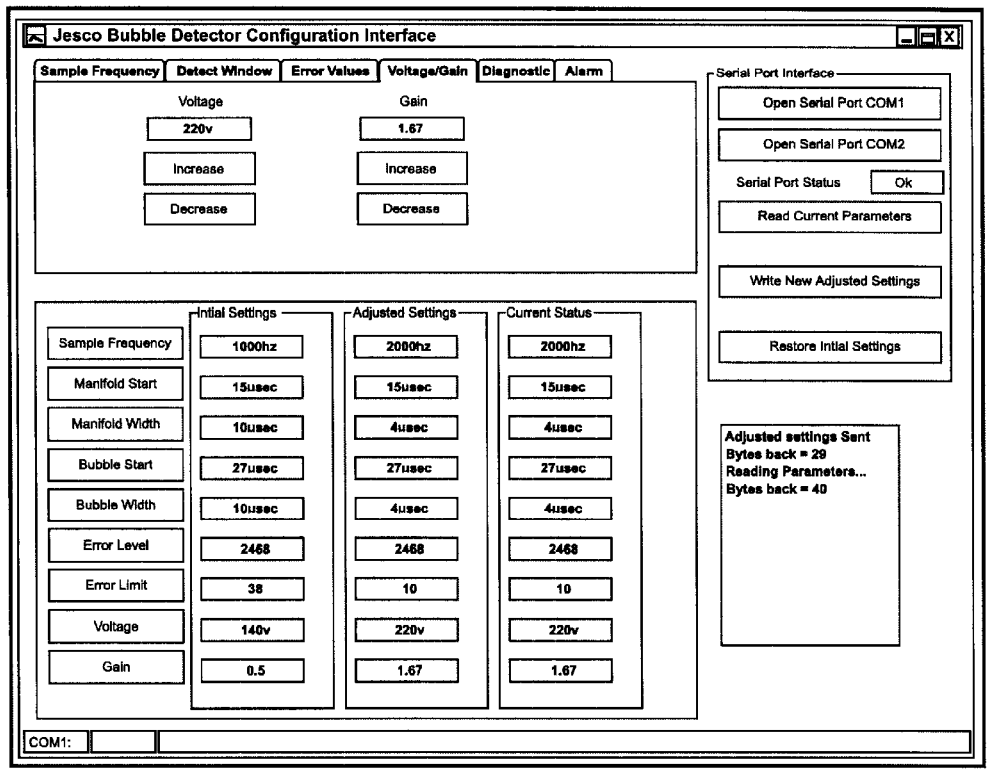
FIG. 29 is a screen shot of the bubble detector interface software of FIG. 24 with voltage/gain selected for display.
Figure 30:
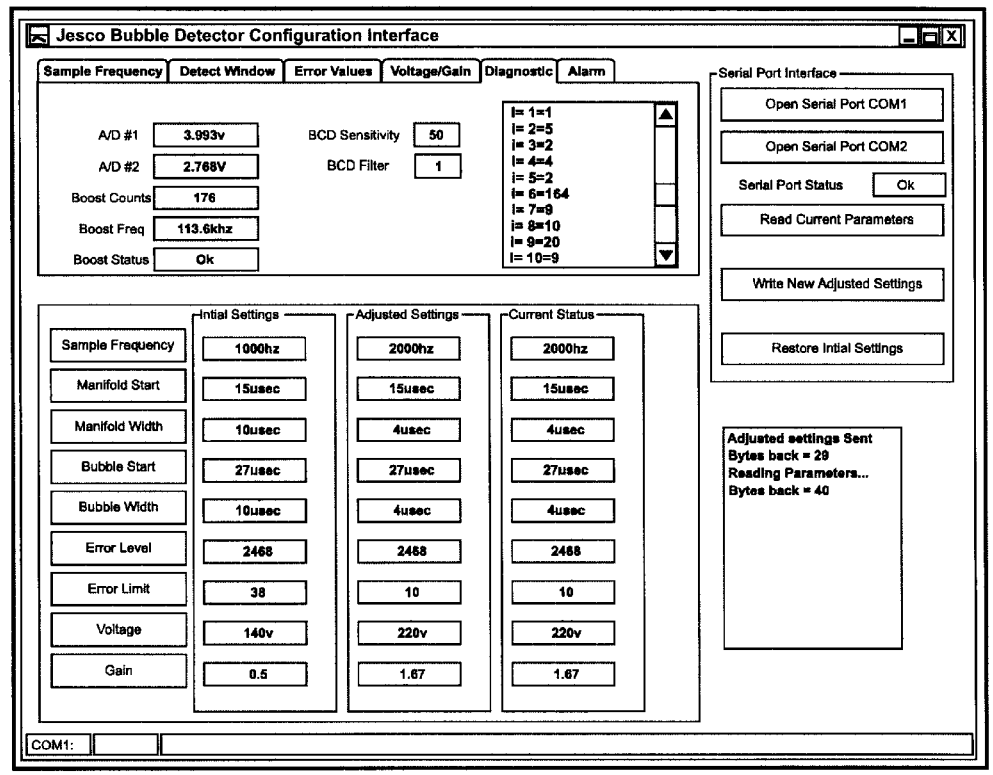
FIG. 30 is a screen shot of the bubble detector interface software of FIG. 24 with diagnostics selected for display.
Figure 31:
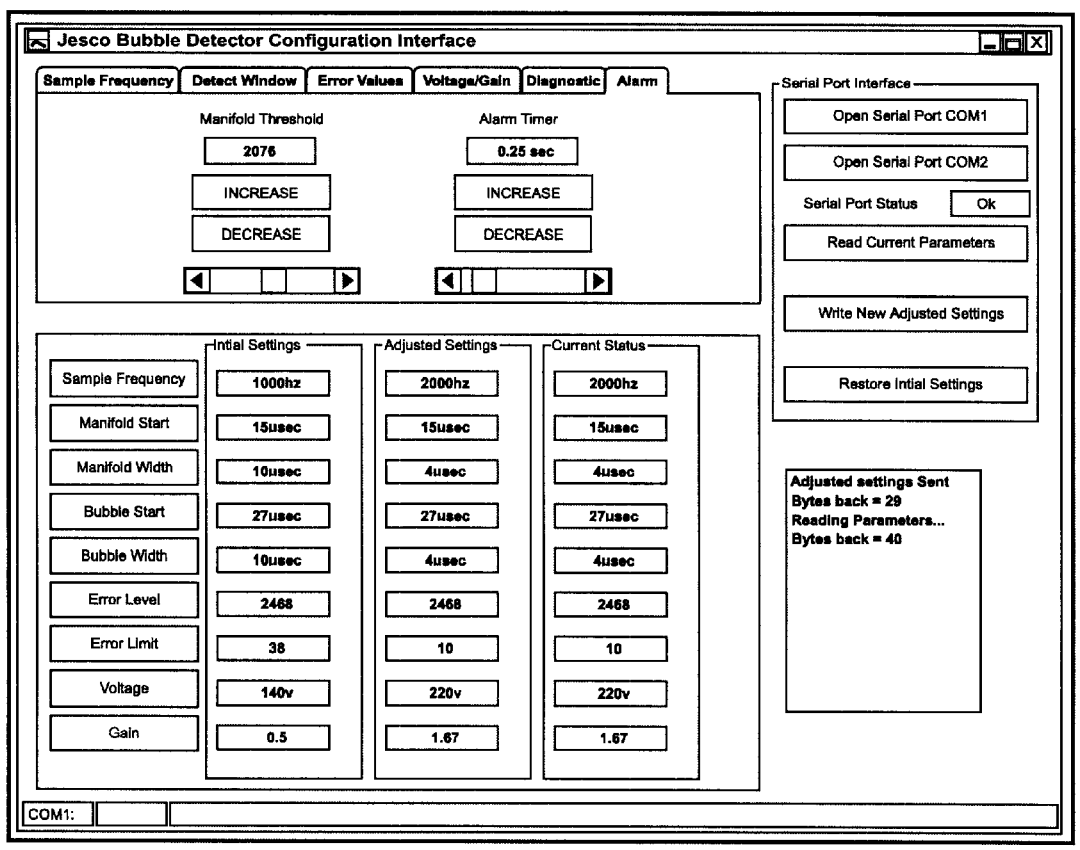
FIG. 31 is a screen shot of the bubble detector interface software of FIG. 24 with alarm data selected for display.

To properly view and adjust these windows an oscilloscope with at least 2 channels is connected to the control module 24. A channel 1 probe is connected to a TPWF (waveform) test point and a channel 1 probe ground is connected to a DGND test point. A channel 2 probe is connected to a TPB (Blanking Pulse) test point. A typical echo waveform and blanking pulse response will appear as shown in FIG. 27. This scope trace shows three relatively large echoes. The first is the initial response of the transducer 14 to the energy pulse. The oscilloscope should be set to trigger at approximately −8V on the falling edge of this pulse. The first (Manifold) window starts before and is centered about the middle echo. The Second (Bubble) window starts before and is centered about the echo to the far right screen.

To set error levels, limits or values the Error Level or Error Limit Radio Button, or Error Values tabs are selected, respectively. The screen should then resemble the screen shown in FIG. 24.

The Error Level adjustment on the configuration interface screen is a software equivalent to the User Sensitivity rotary BCD Switches on the circuit board and defines the minimum threshold level for sensitivity to bubbles. Higher values equate to increased sensitivity. The system can use either the software Error Level adjustment or the User Sensitivity rotary BCD switches, but not both. Whenever the On Board BCD's are "Enabled", the software Error Level is "Disabled", and vise-versa.

Error level is used in conjunction with the Bubble A/D converter, A/D #2. Practical settings for Error Level (or BCD Sensitivity) are those that yield a value of approximately 50–60% of the A/D #2 value while fluid is flowing through the sensing manifold 18. Also, the P-7211A-Series control module 24 uses an A/D reference voltage of 4.096 v so that each DAC value is equal to 1 milli-volt of signal level.

The Error Limit adjustment on the screen is the software equivalent to the User Filter rotary BCD Switches on the circuit bard and defines the minimum number of continuously scanned samples that have failed to exceed the Error Level or Sensitivity setting. For example, if the Error Limit setting value is 5, then five successive failed samples are required before the system will declare a "Bubble". The system can use either a software Error Limit adjustment or User Filter rotary BCD switch settings, but not both. Whenever the On Board User Filter BCD's are "Enabled", the software Error Limit is "Disabled", and vise-versa.

The user adjustable BCD switches may be "Disabled" from this screen. This will limit adjustments for sensitivity and filter settings to software values only and will prevent unauthorized changes to these values. When illuminated, a red LED over each set of BCD switches indicates when the On Board BCD's are enabled.

When using the On Board BCD switches to control sensitivity, each unit of BCD (from 00 to 99) is a multiple of 40 DAC counts and equates to a sensitivity value of 0–3960 counts as read by the on board processor. For example, a sensitivity of 50 equates to 2000 counts for sensitivity threshold (50 BCD units×40 counts per BCD unit). The Function of the On Board Sensitivity BCD switches is identical to that of the "Error Level" software setting listed above.

The On Board BCD switches that control Filter Level are simple unit values (00 to 99) and are added to an internal value of 1, for an overall range of 1–100. The function of the On Board Filter BCD switches is identical to that of the "Error Limit" software setting listed above.

One primary difference between Software and User settings described above is that the Software adjustments require a PC to change, thereby making the system more tamper resistant to unauthorized changes. Also, the software adjustments for Error (Sensitivity) are made in finer increments (1 mV) than the User BCD switches (40 mV). However, from an operational standpoint, it's very difficult to actually measure the differences as far as "real world sensitivity" is concerned. Any air bubbles sensed usually cause a radical drop in echo.

The Outputs may be set to latch in the "Alarm" state from this screen. If an alarm occurs, it will be latched in this state until a reset is given. Resetting the latched alarm requires either an Input (OPTO 4) to the control module 24 or pushing the Reset Push-button on the lower right-side edge of the control module circuit board shown in FIG. 14.

To, set voltage or gain, the Voltage or Gain Radio Buttons may be selected or the Voltage/Gain tab may be selected. The screen should then resemble the screen shown in FIG. 28.

The voltage setting specifies the voltage level of the pulse to the transducer 14. The voltage setting range=100<Set Point <300 Volts. The gain setting specifies the overall system gain (amplification or attenuation) imposed on the feedback signal echo from the transducer 14 in order to bring the signal level into an acceptable range. The gain setting range is=0.5<Set Point <4.0 (unit less).

In general, pulser Voltage and system Gain should be set to achieve 90 to 100% of the saturation level of the bubble A/D amp, A/D #2. While the system is operating and fluid is moving through the sensing manifold 18, if the A/D #2 value reads at, or above 3.700 v, no adjustment is necessary.

If adjustment is required the gain should first be increased. If a gain adjustment alone does not provide satisfactory levels then pulser voltage should be increased. However, if pulser voltage and Sample Frequency rates are increased indiscriminately, sufficient RMS output power to damage the transducer 14 may result. The RMS power output of the system must be kept below 100 mW (0.100 Watt) or the transducer 14 may be damaged (burned out) due to excessive power.

The Diagnostic display tab provides a tool for monitoring bubble detector assembly 10 performance and for setting alarm threshold values. Upon selecting the diagnostics tab the screen should resemble the screen shown in FIG. 29.

The Diagnostic screen shows the value of the analog to digital converters (A/D #1 & #2), the status of the boost power supply used to pulse the transducer 14s, and the other settings of the system. The A/D #X and Boost values are continually updated approximately every second to the PC. Other values, such as the BCD Sensitivity and Filter switches are only updated whenever a "Write New Adjusted Settings" occurs, or the user presses the "Read Current Parameters" radio button on the right side of the screen.

AID #1 is a measure of echo strength at the front wall 44 of the fluid manifold chamber 30. This value is used primarily to assure that the system is functioning properly. It's position in time is unaffected by the process fluid, but it's amplitude is affected by the process fluid depending on the acoustic impedance of the process fluid. Once the system is set up for a particular application, the value for A/D #1 will remain relatively constant assuming that the transducer 14 is functional and there is a good acoustic coupling between the transducer 14 and acoustic coupling 40.

A/D #2 is a measure of echo strength from the back wall 22 of the fluid chamber 20. This value is compared against the "Error Level" or BCD "Sensitivity" switch settings to determine if a bubble exists, or not. This value is highly dependent on the characteristics of the process fluid being monitored and will likely vary by as much as 20%, depending on the application.

The Boost Status indicator monitors the pulser power output to the transducer 14 to guarantee that the voltage is at the preset value thus preventing excessive output voltage to the transducer 14. It also shuts down the pulser in the event of an electrical short circuit to help prevent damage to the pulser power supply and drive electronics.

An Alarm screen is accessible by pressing the top Right (Alarm) tab. The screen should then resemble the screen shown in FIG. 30.

The Manifold Threshold setting is used with A/D #1 to determine if the system is functioning normally and if there is good acoustic coupling between the transducer 14 and the fluid manifold 18. If the value of A/D #1 is not above the Manifold Threshold setting, the system will turn off the "System OK" outputs and will be considered faulted. This could happen if the Transducer 14 has been damaged, disconnected or loosened from the fluid manifold 18. Since the value of A/D #1 is relatively unaffected by the process fluid it is advisable to set the Manifold Threshold value at about 90–95% of the A/D #1 value.

The Alarm Timer feature is an off delay timer that controls the on time of the system outputs. It functions as an on board "Pulse Stretcher" and is useful to insure that the outputs remain on long enough to give interface equipment adequate time to "see" bubble alarms.

The following is a listing of the 'C' source code for the bubble detector assembly 10:

```
#include <16f876.H>
#define VERSIONID 0x51 // jesco04.c
//-----------------------------------------------------------
// file:        jesco05.c
// description: This is the 'C' source code for the Jesco
//              glue bubble detector.
// author:      EMICROS - Embedded Micro Software
// last update:    3/7/01
// Copyright 2000,2001 Emicros
//
// Jesco06 3/31/01 Fixed Timer2 to interrupt every 10 msec.
// Jesco05 3/7/01 Relaxed the freq table.
//-----------------------------------------------------------
// <21 << Notes >>>>
//
// Instruction Cycle Times: Most instructions take 1 cycle except
// branch instructions which take 2. 1 cycle is 4 oscillator periods.
//
// At 4 Mhz, 1 instruction cycle is 4 Mhz/4 or 1 microsecond
// At 20 Mhz, 1 instruction cycle is 20 Mhz/4 or 200 nanoseconds
//
//-----------------------------------------------------------
// This software requires the CCS C Compiler to compile.
//
// Program using HS option, no Watchdog, No Brownout
//-----------------------------------------------------------
//
//      U9 '175 Bit Assignments
//      -----------------------
//      D0: 0 = SYS_OK_RELAY and SYS_OK_RLED are OFF
//          1 = SYS_OK_RELAY and SYS_OK_RLED are ON
//
//      D1: 0 = ALARM_RELAY and ALARM_RLED are OFF
//          1 = ALARM_RELAY and ALARM_RLED are ON
//
//      D2: 0 = SYS_OK_OPTO is OFF
//          1 = SYS_OK_OPTO is ON
//
//      D3: 0 = ALARM_OPTO is OFF
```

-continued

```
//          1 = ALARM_OPTO is ON
//
// SYS_OK_RELAY, SYS_OK_RLED, and SYS_OK_OPTO are
ON if no error,
// OFF if error (D0 and D2).
//
// ALARM ENABLE SWITCH:
//      Switch set to OFF Position:
//      In this position the the 'alarmmode' is ALARM_OFF
//      and the
//
//-----------------------------------------------------------
#define WAITING4START 0
#define WAITING4DATA 1
#define PROCESSBINARYCOMMAND 2
#define READBINARYBUFFER 3
#define STARTBINARYCOMMAND    0xf0
#define BINARYREAD        0xf1
#define BINARYWRITE       0xf2
#define WRITEBUFFER       0xf3
#define BINARYVERSION     0xe0
//-----------------------------------------------------------
// BINARY COMMANDS:
//
// Read Binary Command: Command sent to Jesco to read the buffer
//              stored on EEPROM. Command bytes are echoed
//              and 20 bytes of data returned.
//
// [PC COMMAND —> Jescso] [Jesco Response --> PC]
//   Byte   1    2    1    2    3–32
// BINARYREAD   0xf0   0xf1   0xf0   0xf1   30 bytes of data
//-----------------------------------------------------------
// Write Binary Command: Command and data sent to Jesco to program
//              the 20 byte parameter set stored in EEPROM.
//
// [PC COMMAND —> Jescso] [Jesco Response --> PC]
//   Byte   1    2    1    2    3–32
// BINARYREAD   0xf0   0xf2   0xf0   0xf1   30 bytes of data
//-----------------------------------------------------------
//-----------------------------------------------------------
// Version 0.0jesco00          10/12/00 R. Russ
//
// -Initial version.
//-----------------------------------------------------------
void DebounceRunSetup();
void DebounceReset();
void DebounceExtReset();
void DebounceAlarmEnable();
#use delay(clock=20000000)
//#use delay(clock=8000000)
//#use delay(clock=14745600)
#use rs232(baud=9600, xmit=PIN_C6, rcv=PIN_C7, ERRORS)
#use fast_io(a)
#use fast_io(b)
#use fast_io(c)
#byte PORTA = 5
#byte PORTB = 6
#defineALL_IN      0xff
#defineALL_OUT 0x00
#define PORTCDDR 0x96
#define PORTADDR 0x00
//-----------------------------------------------
// PORTA Signal Definitions
//-----------------------------------------------
#defineBLANK    PIN_A0
#define E138  PIN_A2
#define CSm 0b11000111 // mask
#define CS0 0b00000000
#define CS1 0b00100000
#define CS2 0b00010000
#define CS3 0b00110000
#define CS4 0b00001000
#define CS5 0b00101000
#define CS6 0b00011000
#define CS7 0b00111000
#define SetE1() delay_cycles(4);output_low(E138)
#define ClearE1() output_high(E138)
#define SetCS0() {PORTA&=CSm;PORTA|=CS0;SetE1();}
#define SetCS1() {PORTA&=CSm;PORTA|=CS1;SetE1();}
```

-continued

```
#define SetCS2()  {PORTA&=CSm;PORTA|=CS2;SetE1();}
#define SetCS3()  {PORTA&=CSm;PORTA|=CS3;SetE1();}
#define SetCS4()  {PORTA&=CSm;PORTA|=CS4;SetE1();}
#define SetCS5()  {PORTA&=CSm;PORTA|=CS5;SetE1();}
#define SetCS6()  {PORTA&=CSm;PORTA|=CS6;SetE1();}
#define SetCS7()  {PORTA&=CSm;PORTA|=CS7;SetE1();}
#define SetBLANK() output_low(BLANK)
#define ClearBLANK() output_high(BLANK)
//#byte SPBRG = 0x99    // baud rate generator register
#include <ctype.h>
#include <stdlib.h>
#define NONE      0
#define ERROR     1
#define RESET     2
#define PROCESS   3
#define SETDATA   4
#define CONFIGURE 5
char rs_command = NONE;
#define MAXEE     30
#define NVMVERSION  MAXEE-1
                        // version last eeprom parameter block
#define UBYTE unsigned int
#define UWORD unsigned long
unsigned int_binary_buffer[MAXEE], binary_count,
    x0, x1;
UBYTE     error_count,
          outputs,
          int_occured,
          boost_result,
          boosterrorcount,
          boosterrordb,
          bgpat,
          bgtimer;
UBYTE     switches,      // 8 bit storage location 541 register
percentdetect,           // 8 bit storage location 541 register
misses,                  // 8 bit storage location 541 register
rawpercentdetect,        // 8 bit storage location 541 register
rawmisses,               // 8 bit storage location 541 register
lastpercentdetect,
lastrawmisses,
skip,
debouncerawmisses,
debouncerawpercent,
frequency_index,// 8 bit, array location
          manifold 18start,    //
          manifold 18width,    //
          bubblestart,   //
          bubblewidth,   //
          t2_div,        //
          t2_cnt,        //
          t2_rate,       //
          error_limit,   //
          ee_error_limit,    //
          volts,         //
          gain,          //
          board_bcd_enable,
          tempstatus,    // status output
          result,        // error result
          man_result,    // result of manifold 18 level check
          xresetsw,      // external reset switch status
          xreset_debounce,// external reset switch debounce counter
          resetsw,       // reset switch status
          reset_debounce,    // reset switch debounce counter
          alarmmode,     // alarm enable switch status
          alarm_debounce,    // alarm enable debounce counter
          mode,          // run or setup mode
          mode_debounce, // mode select switch debounce counter
          alarm_latch_timer,  //
          alarm_timer,   //
          latch_error;   //
#define RUN 0
#define SETUP   1
#define OK  0
#define BAD 1
    #define PUSHED    0
    #define RELEASED 1
    #define ALARM_OFF  0
    #define ALARM_ON   1
define DEBOUNCE   25    // 2msec * 25 = 50 msec UWORD    ad1, ad2,      // 16 bit locations for 12 bit a/d readings
         tad1, tad2,    // temp a/d reading for display purposes
         tpulse_CCP1,   // temp pulse reading
         man_error_level,// manifold 18 error level check
         ee_error_level,    // error level check
         error_level;   // error level check
UWORD    frequency;
UWORD    timer1_reset_value;
//------------------------------------------------------------
// isr:       serial_isr()
// description: This isr receives RS232 data and processes the
//              data stream.
//------------------------------------------------------------
#define ESCAPE          0x1b
#define CR              0x0d
#define MAXI2CBUF       64
#define HEX             0
#define DECIMAL         1
char
         inchar,
         readcount,
         rs_state = WAITING4START,
         scmmd;
unsigned int x,
         version;
#define MAXFREQ 81
const UWORD frequency_array[MAXFREQ] = {
    5000,       // index 0 freq=1000 hz
    4762,       // index 1 freq=1050 hz
    4545,       // index 2 freq=1100 hz
    4348,       // index 3 freq=1150 hz
    4167,       // index 4 freq=1200 hz
    4000,       // index 5 freq=1250 hz
    3846,       // index 6 freq=1300 hz
    3704,       // index 7 freq=1350 hz
    3571,       // index 8 freq=1400 hz
    3448,       // index 9 freq=1450 hz
    3333,       // index 10 freq=1500 hz
    3226,       // index 11 freq=1550 hz
    3125,       // index 12 freq=1600 hz
    3030,       // index 13 freq=1650 hz
    2941,       // index 14 freq=1700 hz
    2857,       // index 15 freq=1750 hz
    2778,       // index 16 freq=1800 hz
    2703,       // index 17 freq=1850 hz
    2632,       // index 18 freq=1900 hz
    2564,       // index 19 freq=1950 hz
    2500,       // index 20 freq=2000 hz
    2439,       // index 21 freq=2050 hz
    2381,       // index 22 freq=2100 hz
    2326,       // index 23 freq=2150 hz
    2273,       // index 24 freq=2200 hz
    2222,       // index 25 freq=2250 hz
    2174,       // index 26 freq=2300 hz
    2128,       // index 27 freq=2350 hz
    2083,       // index 28 freq=2400 hz
    2041,       // index 29 freq=2450 hz
    2000,       // index 30 freq=2500 hz
    1961,       // index 31 freq=2550 hz
    1923,       // index 32 freq=2600 hz
    1887,       // index 33 freq=2650 hz
    1852,       // index 34 freq=2700 hz
    1818,       // index 35 freq=2750 hz
    1786,       // index 36 freq=2800 hz
    1754,       // index 37 freq=2850 hz
    1724,       // index 38 freq=2900 hz
    1695,       // index 39 freq=2950 hz
    1667,       // index 40 freq=3000 hz
    1639,       // index 41 freq=3050 hz
    1613,       // index 42 freq=3100 hz
    1587,       // index 43 freq=3150 hz
    1563,       // index 44 freq=3200 hz
    1538,       // index 45 freq=3250 hz
    1515,       // index 46 freq=3300 hz
    1493,       // index 47 freq=3350 hz
    1471,       // index 48 freq=3400 hz
    1449,       // index 49 freq=3450 hz
    1429,       // index 50 freq=3500 hz
    1408,       // index 51 freq=3550 hz
```

```
        1389,      // index 52 freq=3600 hz
        1370,      // index 53 freq=3650 hz
        1351,      // index 54 freq=3700 hz
        1333,      // index 55 freq=3750 hz
        1316,      // index 56 freq=3800 hz
        1299,      // index 57 freq=3850 hz
        1282,      // index 58 freq=3900 hz
        1266,      // index 59 freq=3950 hz
        1250,      // index 60 freq=4000 hz
        1235,      // index 61 freq=4050 hz
        1220,      // index 62 freq=4100 hz
        1205,      // index 63 freq=4150 hz
        1190,      // index 64 freq=4200 hz
        1176,      // index 65 freq=4250 hz
        1163,      // index 66 freq=4300 hz
        1149,      // index 67 freq=4350 hz
        1136,      // index 68 freq=4400 hz
        1124,      // index 69 freq=4450 hz
        1111,      // index 70 freq=4500 hz
        1099,      // index 71 freq=4550 hz
        1087,      // index 72 freq=4600 hz
        1075,      // index 73 freq=4650 hz
        1064,      // index 74 freq=4700 hz
        1053,      // index 75 freq=4750 hz
        1042,      // index 76 freq=4800 hz
        1031,      // index 77 freq=4850 hz
        1020,      // index 78 freq=4900 hz
        1010       // index 79 freq=4950 hz
        1000       // index 80 freq=5000 hz
};
#int_rda
serial_isr()
{
    //----------------------------------------------
    // Read in the received character.
    //----------------------------------------------
    inchar = getc();
//  putc(inchar);      // echo if needed
    switch(rs_state)
    {
    case READBINARYBUFFER:
        binary_buffer[binary_count] = inchar;
        binary_count++;
        if(binary_count >= MAXEE-1)
        {
            rs_state = WAITING4START;
            rs_command = PROCESS;
            scmmd = WRITEBUFFER;
        }
        break;
    case PROCESSBINARYCOMMAND:
        switch(inchar)
        {
        case BINARYREAD:
            rs_state WAITING4START;
            rs_command = PROCESS;
            scmmd = BINARYREAD;
            break;
        case BINARYWRITE:
            rs_state = READBINARYBUFFER;
            binary_count = 0:
            break;
        }
        break;
    case WAITING4START:
        switch(inchar)
        {
        //----------------------------------------------
        // Check for a start binary command
        //----------------------------------------------
        case STARTBINARYCOMMAND:
            rs_state = PROCESSBINARYCOMMAND;
            return;
            break;
        case BINARYVERSION:
            putc(versionid);
            break;
        //----------------------------------------------
        // Check for ASCII commands
        //----------------------------------------------
        //----------------------------------------------
        case '1': case '2':
        case '3': case '4':
        case '5': case '6':
        case 'z':
        case 'a':
        case 'b':
        case 'e':
        case 'p':        // single excite (if in setup)
        case 'r':
        case 's':        // read input switches
        case 'v':        // display version command
            rs_command = inchar;
            break;
        //----------------------------------------------
        // not a legal command.
        //----------------------------------------------
        default: rs_command = ERROR; break;
        }
        rs_state = WAITING4START;
        break;
#if 0
    case WAITING4DATA:
        //----------------------------------------------
        // Check for an escape character. If it is
        // then reset the state.
        //----------------------------------------------
        if(inchar == ESCAPE)
        {
            rs_state WAITING4START;
            rs_command = RESET;
            return;
        }
        //----------------------------------------------
        // Check for a comma that terminates
        // the data field.
        //----------------------------------------------
        if((inchar == ',')||(inchar == CR))
        {
            instr[in_cnt] = 0;      // terminate the string
            if(in_cnt > 0)
                data[data_cnt++] = atoi(instr);
            in_cnt = 0;
            if(inchar == CR)
            {
                rs_state = WAITING4START;
                rs_command = PROCESS;
                return;
            }
        }
        instr[in_cnt] = inchar;
        in_cnt++;
        if(in_cnt >= MAXBUF)
        {
            rs_state = WAITING4START;
            rs_command = RESET;
            return;
        }
        break;
#endif
    }
}
void PrintCR()
{
    printf("[r]");
}
void PrintACK()
{
    printf("!");
}
#define STATUS     3    // register
#defineRP1 6           // bit
#defineRP0 5           // bit
#byte EEDATA = 0x10c
#byte EEADR = 0x10d
#define EECON1     0x18c
#define EECON2     0x18d
#define RD 0           // bit
#define WR 1           // bit
```

-continued

```
#define WREN     2    // bit
#define WRERR    3    // bit
#define EEPGD    7    // bit
#define PIR2 0x0d
#define EEIF4
//#define eeread read_eeprom
#if 1
unsigned int eeread(unsigned int adr)
{
#if 0
    unsigned int er;
#asm
    bsf STATUS,RP1
    bcf STATUS,RP0
#endasm
#asm
    movlw adr
    movwf EEDATA
    bsf STATUS,RP0        // bank 3
    bcf EECON1,EEPGD      // Point to DATA memory
    bsf EECON1,RD // EEPROM read
    bcf STATUS,RP0        // bank 2
    movf    EEDATA,W    // w = eedata
    movwf er
#endasm
    return(er);
#endif
    return(read_eeprom(adr));
}
#endif
//#define eewrite write_eeprom
#if 1
unsigned int eewrite(unsigned int adr, unsigned int dta)
{
    write_eeprom(adr, dta);
    return(eeread(adr));
#if 0
// unsigned int er;
#asm
    bsf STATUS,RP1
    bcf STATUS,RP0
#endasm
    EEADR = adr;
    EEDATA = dta;
#asm
// movf adr,w
// movwf EEADR
// movf dta,w
// movwf EEDATA
    bsf STATUS,RP0         // bank 3
    bcf EECON1,EEPGD       // Point to DATA memory
    bsf EECON1,WREN        // EEPROM write enable
    movlw 0x55             //
    movwf EECON2 // write 55h
    movlw 0xaa             //
    movwf EECON2 // write AAh
    bsf EECON1 ,WR         // EEPROM write enable
#endasm
// delay_ms(50);
#asm
t5:
    bffss   PIR2,EEIF
    goto    t5
    bcf     PIR2,EEIF
    bcf     EECON1,WREN   // EEPROM write enable
#endasm
    return(eeread(adr));
#endif
}
#endif
UBYTE c1,c2,c3;
const UBYTE c2b[16] = {
    0xff,   // 0
    0xff,   // 1
    0xff,   // 2
    9,      // 3
    7,      // 4
    5,      // 5
    3,      // 6
    1,      // 7
    0xff,   // 8
    0xff,   // 9
    0xff,   // a
    8,      // b
    6,      // c
    4,      // d
    2,      // e
    0       // f
};
UBYTE Convert2BCD(UBYTE xt)
{
    swap(xt);
    c1 = xt & 0x0f;
    c2 = xt & 0xf0;
    swap(c2);
    c3 = c2b[c2]*10;
    c3 += c2b[c1];
    return(c3);
}
#define AD1_CS      PIN_C5
#define AD1_SCLK PIN_C3
#define AD1_DATA PIN_C4
#define AD2_CS      PIN_C0
#define AD2_SCLK PIN_A1
#define AD2_DATA PIN_C1
//----------------------------------------------------------
// Define macros to read '541 signals
//----------------------------------------------------------
//#define ReadSwitches() set_tris_b (ALL_IN);\
//      SetCS3();                             \
//      switches = PORTB;                     \
//      ClearE1();
#define ReadDetect() set_tris_b (ALL_IN);\
      SetCS2();                              \
      percentdetect = PORTB;        \
      ClearE1();
#define ReadMisses() set_tris_b (ALL_IN);\
      SetCS0();                  \
      misses = PORTB            \
      ClearE1();
UBYTE ReadSwitches()
{
    set_tris_b (ALL_IN);
    SetCS3();
    switches = PORTB;
    ClearE1();
    return(switches);
}
UBYTE ReadSensitivitySwitches()
{
    set_tris_b (ALL_IN);
    SetCS2();
    percentdetect = PORTB;
    percentdetect = Convert2BCD(percentdetect);
    ClearE1();
    return(percentdetect);
}
UBYTE ReadFilterSwitches()
{
    set_tris_b (ALL_IN);
    SetCS0();
    misses = PORTB;
    misses = Convert2BCD(misses);
    ClearE1();
    return(misses);
}
//----------------------------------------------------------
// Define macro for SCLK toggle. At 20 Mhz, time from high to
// low is 20 nsec (using fastio).
//----------------------------------------------------------
#define SetSCLK1()output_high(AD1_SCLK)
#define ClearSCLK1()      output_low(AD1_SCLK)
#define ToggleSCLK1()     ClearSCLK1();SetSCLK1()
//----------------------------------------------------------
// Define macro for SCLK toggle. At 20 Mhz, time from high to
// low is 20 nsec (using fastio).
//----------------------------------------------------------
#define SetSCLK2()output_high(AD2_SCLK)
```

-continued

```
#define ClearSCLK2()      output_low(AD2_SCLK)
#define ToggleSCLK2()     ClearSCLK2();SetSCLK2()
//---------------------------------------------------------
// function:     StartAD1()
// format:       Start the conversion on A/D #1.
//---------------------------------------------------------
void StartAD1( void)
{
    ClearSCLK1();              // make sure sclk is low
    output_low(AD1_CS);        // start the conversion
    delay_cycles(5);           // 1.0 usec
    delay_cycles(5);           // 2.0 usec
    delay_cycles(5);           // 3.0 usec
    delay_cycles(5);           // 4.0 usec
    delay_cycles(5);           // 5.0 usec
    delay_cycles(5);           // 6.0 usec
    delay_cycles(5);           // 7.0 usec
}
//---------------------------------------------------------
// function:     ReadAD1()
// format:       Read A/D #1.
//---------------------------------------------------------
void ReadAD1(void)
{
#if 0
    ClearSCLK1();              // make sure sclk is low
    output_low(AD1_CS);        // start the conversion
    delay_cycles(5);           // 1.0 usec
    delay_cycles(5);           // 2.0 usec
    delay_cycles(5);           // 3.0 usec
    delay_cycles(5);           // 4.0 usec
    delay_cycles(5);           // 5.0 usec
    delay_cycles(5);           // 6.0 usec
    delay_cycles(5);           // 7.0 usec
#endif
    ad1 = 0;                   // 7.4 usec
    delay_cycles(1);           // 7.6 usec
    SetSCLK1();                // 7.8 usec
//---------------------------------------------------------
// NOTE: Each bit takes 800 nsec to read, 12*800 nsec = 9.6usec total
//---------------------------------------------------------
/* read bit 11 */ ToggleSCLK1(); if(input(AD1_DATA))ad1 |= 0x800;
/* read bit 10 */ ToggleSCLK1(); if(input(AD1_DATA))ad1 |= 0x400;
/* read bit 9  */ ToggleSCLK1(); if(input(AD1_DATA))ad1 |= 0x200;
/* read bit 8  */ ToggleSCLK1(); if(input(AD1_DATA))ad1 |= 0x100;
/* read bit 7  */ ToggleSCLK1(); if(input(AD1_DATA))ad1 |= 0x080;
/* read bit 6  */ ToggleSCLK1(); if(input(AD1_DATA))ad1 |= 0x040;
/* read bit 5  */ ToggleSCLK1(); if(input(AD1_DATA))ad1 |= 0x020;
/* read bit 4  */ ToggleSCLK1(); if(input(AD1_DATA))ad1 |= 0x010;
/* read bit 3  */ ToggleSCLK1(); if(input(AD1_DATA))ad1 |= 0x008;
/* read bit 2  */ ToggleSCLK1(); if(input(AD1_DATA))ad1 |= 0x004;
/* read bit 1  */ ToggleSCLK1(); if(input(AD1_DATA))ad1 |= 0x002;
/* read bit 0  */ ToggleSCLK1(); if(input(AD1_DATA))ad1 |= 0x001;
    ClearSCLK1();              // 200 nsec
    output_high(AD1_CS);       // 200 nsec
// total = 18.2 usec.
}
//---------------------------------------------------------
// function:     StartAD2()
// format:       Start the conversion on A/D #2.
//---------------------------------------------------------
void StartAD2(void)
{
    ClearSCLK2();              // make sure sclk is low
    output_low(AD2_CS);        // start the conversion
    delay_cycles(5);           // 1.0 usec
    delay_cycles(5);           // 2.0 usec
    delay_cycles(5);           // 3.0 usec
    delay_cycles(5);           // 4.0 usec
    delay_cycles(5);           // 5.0 usec
    delay_cycles(5);           // 6.0 usec
    delay_cycles(5);           // 7.0 usec
}
//---------------------------------------------------------
// function:     ReadAD2()
// format:       Read A/D #2.
//---------------------------------------------------------
void ReadAD2(void)
{
```

-continued

```
#if 0
    ClearSCLK2();              // make sure sclk is low
    outputlow(AD2_CS);         // start the conversion
    delay_cycles(5);           // 1.0 usec
    delay_cycles(5);           // 2.0 usec
    delay_cycles(5);           // 3.0 usec
    delay_cycles(5);           // 4.0 usec
    delay_cycles(5);           // 5.0 usec
    delay_cycles(5);           // 6.0 usec
    delay_cycles(5);           // 7.0 usec
#endif
    ad2 = 0;                   // 7.4 usec
    delay_cycles(1);           // 7.6 usec
    SetSCLK2();                // 7.8 usec
/* read bit 11 */ ToggleSCLK2(); if(input(AD2_DATA))ad2 |= 0x800;
/* read bit 10 */ ToggleSCLK2(); if(input(AD2_DATA))ad2 |= 0x400;
/* read bit 9  */ ToggleSCLK2(); if(input(AD2_DATA))ad2 |= 0x200;
/* read bit 8  */ ToggleSCLK2(); if(input(AD2_DATA))ad2 |= 0x100;
/* read bit 7  */ ToggleSCLK2(); if(input(AD2_DATA))ad2 |= 0x080;
/* read bit 6  */ ToggleSCLK2(); if(input(AD2_DATA))ad2 |= 0x040;
/* read bit 5  */ ToggleSCLK2(); if(input(AD2_DATA))ad2 |= 0x020;
/* read bit 4  */ ToggleSCLK2(); if(input(AD2_DATA))ad2 |= 0x010;
/* read bit 3  */ ToggleSCLK2(); if(input(AD2_DATA))ad2 |= 0x008;
/* read bit 2  */ ToggleSCLK2(); if(input(AD2_DATA))ad2 |= 0x004;
/* read bit 1  */ ToggleSCLK2(); if(input(AD2_DATA))ad2 |= 0x002;
/* read bit 0  */ ToggleSCLK2(); if(input(AD2_DATA))ad2 |= 0x001;
    ClearSCLK2();
    output_high(AD2_CS);
}
//---------------------------------------------------------
// function:     ReadEEParameters()
// format:       2 byte values store as LOWBYTE, HIBYTE
//---------------------------------------------------------
void ReadEEParameters(void)
{
    gain                              = eeread(0);
    manifold 18start                  = eeread(1);
    manifold 18width                  = eeread(2);
    bubblestart                       = eeread(3);
    bubblewidth                       = eeread(4);
    *(unsigned int *)&ee_error_level  = eeread(5);
    *(unsigned int *)(&ee_error_level+1) = eeread(6);
    ee_error_limit                    = eeread(7);
    frequency_index                   = eeread(8);
    volts                             = eeread(9);
    board_bcd_enable                  = eeread(10);
    latch_error                       = eeread(11);
    alarm_latch_timer                 = eeread(12);
    *(unsigned int *)&man_error_level = eeread(13);
    *(unsigned int *)(&man_error_level+1) = eeread(14);
    timer1_reset_value = ~frequency_array[frequency_index];
}
void Storeparameters(void)
{
    eewrite(0,gain);
    eewrite(1,manifold 18start);
    eewrite(2,manifold 18width);
    eewrite(3,bubblestart);
    eewrite(4,bubblewidth);
    eewrite(5,*(unsigned int *)&ee_error_level);
    eewrite(6,*(unsigned int *)(&ee_error_level+1));
    eewrite(7,ee_error_limit);
    eewrite(8,frequency_index);
    eewrite(9,volts);
    eewrite(10,board_bcd_enable);
    eewrite(11,latch_error);
    eewrite(12,alarm_latch_timer);
    eewrite(13,*(unsigned int *)&man_error_level);
    eewrite(14,*(unsigned int *)(&man_error_level+1));
}
UBYTE Icmw, Icms;
UBYTE Icbw, Icbs;
//---------------------------------------------------------
// function:  Detect()
// description: This function controls the bubble detection.
//---------------------------------------------------------
void Detect(void)
{
    Icms = manifold 18start;
```

-continued

```
        Icmw = manifold 18width;
        Icbs = bubblestart;
        Icbw = bubblewidth;
        ClearBLANK(); // hold BLANK low
//----------------------------------------
// Set the gain
//----------------------------------------
        set_tris_b(ALL_OUT);
        PORTB = gain;
        SetCS7();
        ClearE1();
//----------------------------------------
// Start the detection phase by setting
// the trigger high, small delay, then
// low.
//----------------------------------------
        PORTB = 0;
        SetCS6();
        ClearE1();
        delay_us(2);
        delay_cycles(4);
        PORTB = volts;
        SetCS6();
        ClearE1();
#if 0 // enable for 1 usec marker
        SetBLANK();
        delay_cycles(4);
        ClearBLANK();
#endif
//----------------------------------------
// Manifold 18 blank time
//----------------------------------------
// The following asm code is optimized to provide a 2 microsec
// delay.
//----------------------------------------
#asm
x1a:
        decfsz   Icms,f
        goto     x1b
        goto     x1e
x1b:
        nop
        goto     x1a
x1e:
        nop
#endasm
//----------------------------------------
// Enable the manifold 18 window.
//----------------------------------------
        SetBLANK();
//----------------------------------------
// Manifold 18 detect window
// The following asm code is optimized to provide a 2 microsec
// increment delay time.
//----------------------------------------
#asm
x2a:
        decfsz   Icmw,f
        goto     x2b
        goto     x2e
x2b:
        nop
        goto     x2a
x2e:
        nop
#endasm
//----------------------------------------
// Start the conversion on A/D #1
//----------------------------------------
        ClearSCLK1();           // make sure sclk is low
        output_low(AD1_CS );    // start the conversion
        delay_cycles(3);        // 1.0 usec
        ClearBLANK();
//----------------------------------------
// Bubble Delay time
//----------------------------------------
// The following asm code is optimized to provide a 2 microsec
// increment delay time.
//----------------------------------------
#asm
x3a:
        decfsz   Icbs,f
        goto     x3b
        goto     x3e
x3b:
        nop
        goto     x3a
x3e:
        nop
#endasm
        SetBLANK();
//----------------------------------------
// Bubble Width Detect time
//----------------------------------------
// The following asm code is optimized to provide a 2 microsec
// increment delay time.
//----------------------------------------
#asm
x4a:
        decfsz   Icbw,f
        goto     x4b
        goto     x4e
x4b:
        nop
        goto     x4a
x4e:
        nop
#endasm
//----------------------------------------
// Start the conversion on A/D #2
//----------------------------------------
        ClearSCLK2();           // make sure sclk is low
        outputlow(AD2_CS);      // start the conversion
        delay_cycles(3);        // 1.0 usec
        ClearBLANK();
//      ReadAD1();
        ad1 = 0
        SetSCLK1();
//----------------------------------------
// NOTE: Each bit takes 800 nsec to read, 12*800nsec = 9.6 usec total
//----------------------------------------
/* read bit 11 */ ToggleSCLK1(); if(input(AD1_DATA))ad1 |= 0x800;
/* read bit 10 */ ToggleSCLK1(); if(input(AD1_DATA))ad1 |= 0x400;
/* read bit 9  */ ToggleSCLK1(); if(input(AD1_DATA))ad1 |= 0x200;
/* read bit 8  */ ToggleSCLK1(); if(input(AD1_DATA))ad1 |= 0x100;
/* read bit 7  */ ToggleSCLK1(); if(input(AD1_DATA))ad1 |= 0x080;
/* read bit 6  */ ToggleSCLK1(); if(input(AD1_DATA))ad1 |= 0x040;
/* read bit 5  */ ToggleSCLK1(); if(input(AD1_DATA))ad1 |= 0x020;
/* read bit 4  */ ToggleSCLK1(); if(input(AD1_DATA))ad1 |= 0x010;
/* read bit 3  */ ToggleSCLK1(); if(input(AD1_DATA))ad1 |= 0x008;
/* read bit 2  */ ToggleSCLK1(); if(input(AD1_DATA))ad1 |= 0x004;
/* read bit 1  */ ToggleSCLK1(); if(input(AD1_DATA))ad1 |= 0x002;
/* read bit 0  */ ToggleSCLK1(); if(input(AD1_DATA))ad1 |= 0x001;
        ClearSCLK1();           // 200 nsec
        output_high(AD1_CS);    // 200 nsec
//      ReadAD2();
        ad2
        SetSCLK2();
/* read bit 11 */ ToggleSCLK2(); if(input(AD2_DATA))ad2 |= 0x800;
/* read bit 10 */ ToggleSCLK2(); if(input(AD2_DATA))ad2 |= 0x400;
/* read bit 9  */ ToggleSCLK2(); if(input(AD2_DATA))ad2 |= 0x200;
/* read bit 8  */ ToggleSCLK2(); if(input(AD2_DATA))ad2 |= 0x100;
/* read bit 7  */ ToggleSCLK2(); if(input(AD2_DATA))ad2 |= 0x080;
/* read bit 6  */ ToggleSCLK2(); if(input(AD2_DATA))ad2 |= 0x040;
/* read bit 5  */ ToggleSCLK2(); if(input(AD2_DATA))ad2 |= 0x020;
/* read bit 4  */ ToggleSCLK2(); if(input(AD2_DATA))ad2 |= 0x010;
/* read bit 3  */ ToggleSCLK2(); if(input(AD2_DATA))ad2 |= 0x008;
/* read bit 2  */ ToggleSCLK2(); if(input(AD2_DATA))ad2 |= 0x004;
/* read bit 1  */ ToggleSCLK2(); if(input(AD2_DATA))ad2 |= 0x002;
/* read bit 0  */ ToggleSCLK2(); if(input(AD2_DATA))ad2 |= 0x001;
        ClearSCLK2();
        output_high(AD2_CS);
        if(ad1 < man_error_level)
            man_result = BAD;
        else
            man_result = OK;
        if(ad2 < error_level)
        {
```

```
            if(error_count > error_limit)
               result = BAD;
            else
               error_count++;
         }
         else
         {
            error_count = 0;
            if(latch_error == FALSE)
               result = OK;
         }
      }
}
UWORD last_CCP1, now_CCP1, pulse_CCP1, save_CCP1;
UBYTE CCP1_state;
#define W4FIRSTEDGE    0
#define CCP1_VALID     1
#int_ccp1
ccp1_isr()
{
   now_CCP1 = CCP_1
   if(int_occurred == TRUE)
   {
      CCP1_state = W4FIRSTEDGE;
   }
   else
   {
      if(CCP1_state == W4FIRSTEDGE)
      {
         last_CCP1 = now_CCP1;
         CCP1_state = CCP1_VALID;
      }
      else
      {
         pulse_CCP1 = now_CCP1-last_CCP1;
         last_CCP1 = now_CCP1;
      }
   }
   int_occurred = FALSE;   // clear the indicator flag
}
#define GAP 30
#define MP 1
const UWORD pulse_hi[6] = {    MP*(427+GAP), // 100 volt
                               MP*(319+GAP),   // 140 volt
                               MP*(240+GAP),   // 180 volt
                               MP*(196+GAP),   // 220 volt
                               MP*(171+GAP),   // 260 volt
                               MP*(152+GAP)    // 300 volt
                          }
const UWORD pulse_lo[6] = {    MP*(327-GAP),   // 100 volt
                               MP*(244-GAP),   // 140 volt
                               MP*(200-GAP),   // 180 volt
                               MP*(175-GAP),   // 220 volt
                               MP*(153-GAP),   // 260 volt
                               MP*(135-GAP)    // 300 volt
                          }
#if 0
const UWORD pulse_hi[6] = {    427, // 100 volt
                               319,    // 140 volt
                               240,    // 180 volt
                               196,    // 220 volt
                               171,    // 260 volt
                               152     // 300 volt
                          }
const UWORD pulse_lo[6] = {    327, // 100 volt
                               244,    // 140 volt
                               200,    // 180 volt
                               175,    // 220 volt
                               153,    // 260 volt
                               135     // 300 volt
                          }
#endif
UBYTE CheckBoostMonitor(void)
{
   switch(volts)
   {
      // 100 volts
      case 2:if(tpulse_CCP1 > pulse_hi[0]) return ERROR;
             if(tpulse_CCP1 < pulse_lo[0]) return ERROR;
             return OK;
      // 140 volts
      case 3:if(tpulse_CCP1 > pulse_hi[1]) return ERROR;
             if(tpulse_CCP1 < pulse_lo[1]) return ERROR;
             return OK;
      // 180 volts
      case 8:if(tpulse_CCP1 > pulse_hi[2]) return ERROR;
             if(tpulse_CCP1 < pulse_lo[2]) return ERROR;
             return OK;
      // 220 volts
      case 9:if(tpulse_CCP1 > pulse_hi[3]) return ERROR;
             if(tpulse_CCP1 < pulse_lo[3]) return ERROR;
             return OK;
      // 260 volts
      case 10:if(tpulse_CCP1 > pulse_hi[4]) return ERROR;
              if(tpulse_CCP1 < pulse_lo[4]) return ERROR;
              return OK;
      // 300 volts
      case 11:if(tpulse_CCP1 > pulse_hi[5]) return ERROR;
              if(tpulse_CCP1 < pulse_lo[5]) return ERROR;
              return OK;
   }
}
#define ALARM_OPTO      0x08
#define ALARM_RELAY     0x02
#define SYS_OK_OPTO     0x04
#define SYS_OK_RELAY    0x01
#int_timer2
timer2_isr()
{
   //-----------------------------------------
   // Update Alarm
   //-----------------------------------------
   if(result == BAD)
   {
      alarm_timer = alarm_latch_timer
      //-----------------------------------------
      // if ALARM is ENABLED
      //    ALARM_RELAY, ALARM_RLED, ALARM_OPTO = ON
      //    (d1=d3=1)
      //-----------------------------------------
      tempstatus = 0;
      if(alarmmode == ALARM_ON)
         tempstatus = ALARM_OPTO | ALARM_RELAY;
   }
   else
   {
      //-----------------------------------------
      // ALARM_RELAY, ALARM_RLED, ALARM_OPTO = OFF
      //    (d1=d3=0)
      //-----------------------------------------
      tempstatus = 0x00;
      if(alarm_timer)
      {
         alarm_timer--;
         if(alarmmode == ALARM_ON)
            tempstatus = ALARM_RELAY;
      }
   }
   //-----------------------------------------
   // Update Sys Ok
   //-----------------------------------------
// if(man_result != BAD)
   if((boost_result != ERROR) & (man_result != BAD))
      //-----------------------------------------
      // SYS_OK_RELAY, SYS_RLED, SYS_OK_OPTO = ON
      //    (d0=d2=1)
      //-----------------------------------------
      tempstatus |= SYS_OK_RELAY | SYS_OK_OPTO;
   set_tris_b(ALL_OUT);
   PORTB = tempstatus;
   SetCS5();
   delay_cycles(12);
   ClearE1();
}
//-----------------------------------------------------------
// isr       Timer1 Interrupt Service Routine
//-----------------------------------------------------------
#int_timer1
timer1_isr()
```

-continued

```
{
    set_timer1 (timer1_reset_value);
    int_occured = TRUE;   // indicate an detect interrupt occured
    //---------------------------------------------
    // Execute the detection algorithm
    //---------------------------------------------
    if((boost_result == OK) && (skip == 0))
       Detect();
    else
    {
       if(skip)
          skip-;
       set_tris_b(ALL_OUT);
       PORTB = volts;
       SetCS6();
       ClearE1();
    }
    //---------------------------------------------
    // Display the bcd enable status
    //---------------------------------------------
    set_tris_b(ALL_OUT);
    PORTB = board_bcd_enable;
    SetCS4();
    delay_cycles(2);
    ClearE1();
    //---------------------------------------------
    // Read the switches for debounce in the
    // background loop
    //---------------------------------------------
    set_tris_b(ALL_IN);
    SetCS3();
    switches = PORTB;
    ClearE1();
    SetCS2();
    rawpercentdetect = PORTB;
    ClearE1();
    SetCS0();
    rawmisses = PORTB;
    ClearE1();
}
//------------------------------------------------------
// Debug routine to set voltage if in setup mode
//------------------------------------------------------
void OutputVolts(UBYTE tv)
{
    if(mode == SETUP)
    {
       volts = tv;
       set_tris_b(ALL_OUT);
       PORTB = volts;
       SetCS6();
       ClearE1();
       printf("V%d", volts);printCR();
    }
    rs_command = NONE;
}
UWORD te;
void SetErrorValues()
{
    if(board_bcd_enable & 0x01)
       error_limit = misses;
    else
       error_limit = ee_error_limit;
    if(board_bcd_enable & 0x02)
    {
       te = percentdetect;
       te *= 40;
       error_level = te;
    }
    else
       error_level = ee_error_level;
}
//------------------------------------------------------
// routine:    main()
// description: This function provides the background processing.
//------------------------------------------------------
void main()
{
    delay_ms(10);
```

-continued

```
    readcount = 0;
    error_count = 0;
    //---------------------------------------------
    // Configure the i/o
    //---------------------------------------------
    set_tris_a(PORTADDR);
    set_tris_b(ALL_IN);   // set data direction to input
    set_tris_c(PORTCDDR);
    ClearBLANK();   // hold BLANK low
    /******************************************
     * update the configuration
     ******************************************/
    version = eeread(NVMVERSION);
    if(version != VERSIONID)
    {
    for(x=0; x<MAXEE-1; x++)
       eewrite(x,0);
    //---------------------------------------------
    // Store the version and read it back.
    //---------------------------------------------
    eewrite(NVMVERSION, VERSIONID);
    version = eeread(NVMVERSION);
    gain = 4;
    manifold18start = 5;
    manifold18width = 5;
    bubblestart = 10;
    bubblewidth = 5;
    ee_error_level = 2000;
    ee_error_limit = 100;
    frequency_index = 0;
    volts = 2;
    board_bcd_enable = 0;
    latch_error = FALSE;
    alarm_latch_timer = 10;
    man_error_level = 300;
    Storeparameters();
    }
    ReadEEParameters();
    //---------------------------------------------
    // Set timer2 to interupt every 10 millisec
    // 1/(20000000/4)/16 = 1/312500 = 3.2 usec
    // overflow: 3.2 usec * 250 = 800 usec
    // interrupt: 800 usec * 12 = 10 millisec
    //
    // 1/(14745600/4)/4 = 1/921600 = 1.085 usec
    // overflow: 1.085 usec * 184 = 200 usec
    // interrupt: 200 usec * (9 + 1) = 1 millisec
    //---------------------------------------------
    setup_timer_2(T2_DIV_BY_16, 250, 12);
    setup_timer_1(T1_INTERNAL | T1_DIV_BY_1);
    // setup_ccp1(CCP_CAPTURE_DIV_16);
    setup_ccp1(CCP_CAPTURE_DIV_4);
    //---------------------------------------------
    // Set the high voltage
    //---------------------------------------------
    set_tris_b(ALL_OUT);
    PORTB = volts;
    SetCS6();
    ClearE1();
    delay_ms(100); // small delay
    ReadSensitivitySwitches();
    ReadFilterSwitches();
    SetErrorValues();
    percentdetect = Convert2BCD(rawpercentdetect);
    misses = Convert2BCD(rawmisses);
    bgtimer = 0;
    outputs = 0;
    mode_debounce = 0;       // reset mode select debounce switch
    mode = SETUP;    // initial mode
    alarm_debounce = 0;       // alarm enable debounce switch
    alarmmode = ALARM_OFF;// initial alarm mode
    reset_debounce = 0;       // reset debounce switch
    resetsw = RELEASED;       // initial mode is release
    xreset_debounce = 0;       // external reset debounce switch
    xresetsw = RELEASED; // external initial mode is release
    error_count = 0;
    result = OK;
    boosterrorcount = 0;
    boosterrordb = 20;
```

-continued

```
CCP1_state = W4FIRSTEDGE;
now_CCP1 = last_CCP1 = pulse_CCP1 = 0;
//---------------------------------------------
// enable the global interrupt and the rs232
// receive data interrupt.
//---------------------------------------------
enable_interrupts(int_rda);
enable_interrupts(int_timer1);
enable_interrupts(int_timer2);
enable_interrupts(int_ccp1);
enable_interrupts(GLOBAL);
//---------------------------------------------
// Background Processing.
//---------------------------------------------
while(1)
{
    set_tris_a(PORTADDR);
    set_tris_b(ALL_OUT);
    set_tris_c(PORTCDDR);
    //---------------------------------------------
    // Small delay to allow some 'debounce' timing
    //---------------------------------------------
    delay_ms(2);
    disable_interrupts(GLOBAL);
    tpulse_CCP1 = pulse_CCP1;
    enable_interrupts(GLOBAL);
    if(CheckBoostMonitor() == BAD)
    {
        if(boosterrordb)
            boosterrordb-;
        else
            boost_result = BAD;
    }
    else
    {
        boosterrordb = 20;
        boost_result = OK;
    }
    SetErrorValues();
    DebounceRunSetup();
    DebounceReset();
    DebounceExtReset();
    DebounceAlarmEnable();
    //---------------------------------------------
    // Debounce the BCD switches
    //---------------------------------------------
    if(rawpercentdetect != lastpercentdetect)
        debouncerawpercent = 50;
    lastpercentdetect = rawpercentdetect;
    if(debouncerawpercent == 0)
        percentdetect = Convert2BCD(rawpercentdetect);
    else
        debouncerawpercent-;
    //---------------------------------------------
    // Debounce the BCD switches
    //---------------------------------------------
    if(rawmisses != lastrawmisses)
        debouncerawmisses 50;
    lastrawmisses = rawmisses;
    if(debouncerawmisses == 0)
        misses = Convert2BCD(rawmisses);
    else
        debouncerawmisses-;
    if(mode == SETUP)
    {
        error_count = 0;
        result = OK;
    }
    switch(rs_command)
    {
        //---------------------------------------------
        // Display constants
        //---------------------------------------------
        case 'e':
            printCR();
            printf("    gain . . . %d", gain); printCR();
            printf("manifold 18start . . . %d", manifold 18start); printCR();
            printf("manifold 18width . . . %d", manifold 18width); printCR();
            printf(" error_level . . . %Iu", error_level); printCR();
            printf(" error_limit . . . %u", error_limit); printCR();
            rs_command = NONE;
            break;
        //---------------------------------------------
        // Display Boost Monitor
        //---------------------------------------------
        case 'b':
            printCR();
            printf(" now . . . %Iu", now_CCP1); printCR();
            printf("last . . . %Iu", last_CCP1); printCR();
            printf("pulse . . . %Iu", pulse_CCP1); printCR();
            printf("state . . . %u", CCP1_state); printCR();
            rs_command = NONE;
            break;
        //---------------------------------------------
        // Display switch inputs information
        //---------------------------------------------
        case 's':
            printf("Percent(Raw) . . . %2x", rawpercentdetect);
            printcR();
            printf("    Inputs . . . %2x", switches);
            printCR();
            printf(" Sensitivity . . . %d", ReadSensitivitySwitches());
            printCR();
            printf("     Filter . . . %d", ReadFilterSwitches());
            printCR();
            rs_command = NONE;
            break;
        //---------------------------------------------
        // Set Voltage Levels
        //---------------------------------------------
        case '1': OutputVolts(2); break;
        case '2': OutputVolts(3); break;
        case '3': OutputVolts(8); break;
        case '4': OutputVolts(9); break;
        case '5': OutputVolts(10); break;
        case '6': OutputVolts(11); break;
        //---------------------------------------------
        // Single excitation if in setup
        //---------------------------------------------
        case 'p':   if(mode == SETUP)
                    {
                        disable_interrupts(GLOBAL);
                        for( x=0; x<1; x++)
                        Detect();
                        printf("P"); printCR();
                    }
        //---------------------------------------------
        // Display a/d information
        //---------------------------------------------
        case 'a':
            disable_interrupts(GLOBAL);
            tad1 = ad1;
            tad2 = ad2;
            enable_interrupts(GLOBAL);
            printCR();
            printf("ad1 = %Id", tad1); printCR();
            printf("ad2 = %Id", tad2); printCR();
            printf("el = %Id", error_level); printCR();
            if(result == BAD)
                printf("BAD");
            else
                printf("OK");
            printcR();
            rs_command = NONE;
            break;
        //---------------------------------------------
        // Display a/d information
        //---------------------------------------------
        case 'z':
            disable_interrupts(GLOBAL);
            tad1 = ad1;
            tad2 = ad2;
            enable_interrupts(GLOBAL);
            putc(*(unsigned int *)&tad1);
            putc(*(unsigned int *)(&tad1+1));
            putc(*(unsigned int *)&tad2);
            putc(*(unsigned int *)(&tad2+1));
            rs_command = NONE;
```

-continued

```
                break;
//----------------------------------------
// Display version information
//----------------------------------------
        case 'v':
                printcR();
                printf("Jesco Ver %d", version);
                rs_command = NONE;
                break;
//----------------------------------------
// Read EEPROM data
//----------------------------------------
        case 'r':
                for(x=0; x<MAXEE; x++)
                {
                  printf("%d", eeread(x));
                  printcR();
                }
                printCR();
                rs_command = NONE;
                break;
        case ERROR:    puts("Command Invalid!");
                       rs_command = NONE;
                       break;
        case RESET:    puts("Resetting . . . ");
                       rs_command = NONE;
                       break;
        case SETDATA:
                       puts("Set Data . . . ");
                       rs_command = NONE;
            break;
        case PROCESS:
            switch(scmmd)
            {
            case BINARYREAD:
                disable_interrupts(GLOBAL);
                tad1 = ad1;
                tad2 = ad2;
                tpulse_CCP1 pulse_CCP1;
                enable_interrupts(GLOBAL);
                for(x=0; x<MAXEE; x++)
                {
                putc(eeread(x));
                }
                putc(*(unsigned int *)&tad1);
                putc(*(unsigned int *)(&tad1+1));
                putc(*(unsigned int *)&tad2);
                putc(*(unsigned int *)(&tad2+1));
                putc(*(unsigned int *)&tpulse_CCP1);
                putc(*(unsigned int *)(&tpulse_CCP1+1));
                putc(boost_result);
                putc(misses);
                putc(percentdetect);
                putc(result);
                break;
            case WRITEBUFFER:
                disable_interrupts(GLOBAL);
                for(x=0; x<MAXEE-1; x++)
                {
//----------------------------------------
// write only if different
//----------------------------------------
                if(eeread(x) != binary_buffer[x])
                  eewrite(x, binary_buffer[x]);
                putc(binary_buffer[x]);
//              putc(eeread(x));
                }
                skip = 200;
                ReadEEParameters();
                enable_interrupts(GLOBAL);
                break;
            }
            rs_command = NONE;
            break;
        }
    }
}
void DebounceRunSetup()
{
//----------------------------------------
// Debounce the run/setup switch
//----------------------------------------
    if(mode == SETUP)
    {
      if((switches & 0x40) == 0x40)
      {
        if(mode_debounce > DEBOUNCE)
        {
          mode_debounce = 0;
          mode = RUN;
        }
        else
          mode_debounce++;
      }
      else
        mode_debounce = 0;
    }
    else
    {
      if((switches & 0x40) == 0x00)
      {
        if(mode_debounce > DEBOUNCE)
        {
          mode_debounce = 0;
          mode = SETUP;
        }
        else
          mode_debounce++;
      }
      else
        mode_debounce = 0;
    }
}
void DebounceAlarmEnable()
{
//----------------------------------------
// Debounce the alarm enable
//----------------------------------------
    if(alarmmode == ALARM_ON)
    {
      if((switches & 0x20) == 0x20)
      {
        if(alarmdebounce > DEBOUNCE)
        {
          alarm_debounce = 0;
          alarmmode = ALARM_OFF;
        }
        else
          alarm_debounce++;
      }
      else
        alarm_debounce = 0;
    }
    else
    {
      if((switches & 0x20) == 0x00)
      {
        if(alarm_debounce > DEBOUNCE)
        {
          alarm_debounce = 0;
          alarmmode = ALARM_ON;
        }
        else
          alarm_debounce++;
      }
      else
        alarm_debounce = 0;
    }
}
void DebounceReset()
{
//----------------------------------------
// Debounce the reset switch
//----------------------------------------
    if(resetsw == PUSHED)
    {
       error_count = 0;
       boost_result = OK,
```

-continued

```
        result = OK;
        if((switches & 0x80) == 0x80)
        {
          if(reset_debounce > DEBOUNCE)
          {
            reset_debounce = 0;
            resetsw = RELEASED;
          }
          else
            reset_debounce++;
        }
        else
          reset_debounce = 0;
      }
      else
      {
        if((switches & 0x80) == 0x00)
        {
          if(reset_debounce > DEBOUNCE)
          {
            reset_debounce = 0;
            resetsw = PUSHED;
          }
          else
            reset_debounce++;
        }
        else
          reset_debounce = 0;
      }
}
#define XRESETMASK 0x02
void DebounceExtReset()
{
    //---------------------------------------------
    // Debounce the reset switch
    //---------------------------------------------
    if(xresetsw == PUSHED)
    {
      error_count = 0;
      result = OK;
      if((switches & XRESETMASK) == XRESETMASK)
      {
        if(xreset_debounce > DEBOUNCE)
        {
          xreset_debounce = 0;
          xresetsw = RELEASED;
        }
        else
          xreset_debounce++;
      }
      else
        xreset_debounce = 0;
    }
    else
    {
      if((switches & XRESETMASK) == 0x00)
      {
        if(xreset_debounce > DEBOUNCE)
        {
          xreset_debounce = 0;
          xresetsw = PUSHED;
        }
        else
          xreset_debounce++;
      }
      else
        xreset_debounce = 0;
    }
}
```

The anomaly detecting assembly 10 is adaptable to virtually any dispensing System. The assembly 10 is compact, inline mounted, and includes a fluid manifold 18 constructed of stainless steel and corrosion resistant, high strength engineered plastic. The design allows easy connection to many fluid systems with little pressure losses. The assembly 10 includes pin connected power and interface receptacles and runs on 90–260 VAC @ 50/60 Hz operating power. The assembly 10 also includes two isolated SPDT relay (DRY) alarm contacts, two isolated and Opto 22 standard output modules for customer interface and two isolated, Opto 22 standard input modules for customer interface. The assembly 10 supports interface voltages specified by the customer at time of order and includes a simple interface to automation, and board level sensitivity adjustments that are mounted inside the control panel 12 to minimize tampering. The assembly 10 also includes internal diagnostics and alarms for Transducer 14 malfunction, broken connections or short circuits of the coaxial cable 16.

A typical application for the assembly 10 is in automotive glass adhesive application systems. The assembly 10 would, in such an application, provide an alarm output whenever it senses air bubbles that could cause an incomplete seal around the glass perimeter and a leak point for air and water. In such an application, the assembly 10 would readily detect air bubbles as fine as ¼" diameter (nom.) spherical voids within a bead at manifold 18 pressures up to 500 PSI. Higher system pressures may diminish the ability of the assembly 10 to sense such fine bubbles, though it is still possible to detect bubbles as fine as ½" diameter (nom) spherical voids within a bead at manifold 18 pressures of 1000 PSI or more.

This description is intended to illustrate certain embodiments of the invention rather than to limit the invention. Therefore, it uses descriptive rather than limiting words.

Obviously, it's possible to modify this invention from what the description teaches. Within the scope of the claims, one may practice the invention other than as described.

What is claimed is:

1. A sealant stream anomaly detecting assembly for detecting anomalies such as gas bubbles in a high-pressure sealant stream, the assembly comprising:
    an ultrasonic transducer supported on a manifold defining a sensing chamber portion of a fluid channel, the transducer being configured to convert electrical input voltage pulses into ultrasonic acoustic energy pulses and to propagate the acoustic energy pulses through the manifold and into the sensing chamber, the transducer also being configured to receive resulting echo pulses from a back wall of the sensing chamber and to convert the echo pulses into electrical output impulses;
    a control module including drive electronics connected to the transducer, the module configured to receive the electrical output impulses from the transducer and to detect diminished and lost echo pulses by comparing the output impulse strength values for a given fluid passing through the sensing chamber to a known output impulse strength value for that same type of fluid having no anomalies;
    an anomaly indicator connected to the control module and configured to flag a user in response to a signal from the control module indicating that the assembly has detected an anomaly such as a bubble in a fluid stream passing through the fluid channel; and the transducer having a flat front active emitter surface that lies flat against a flat manifold outer surface to provide superior acoustic energy pulse coverage throughout the sensing chamber and to avoid having to machine a matching curvature.

2. A sealant stream anomaly detecting assembly as defined in claim 1 in which the back wall of the sensing chamber is disposed generally parallel to the flat front emitter surface of the transducer.

3. A sealant stream anomaly detecting assembly as defined in claim 1 in which the manifold includes an acoustic coupling disposed between the transducer and the back wall of the sensing chamber, the acoustic coupling defining a front wall of the sensing chamber parallel to and opposite the back wall and a pair of side walls of the sensing chamber disposed perpendicular to and connecting the front and back walls.

4. A sealant stream anomaly detecting assembly as defined in claim 3 in which the back wall of the sensing chamber is defined by a flat axial inner end surface of an access plug.

5. A sealant stream anomaly detecting assembly as defined in claim 4 in which the acoustic coupling and access plug are supported in a coaxially abutting relationship within a cylindrical manifold housing.

6. A sealant stream anomaly detecting assembly as defined in claim 5 in which the transducer is supported in an abutting relationship with the acoustic coupling by a transducer housing that is supported on an upper end of the manifold housing.

7. A sealant stream anomaly detecting assembly as defined in claim 6 in which a spring disposed between the transducer and the transducer housing and configured to absorb acoustic coupling expansion, deflection or distortion.

8. A sealant stream anomaly detecting assembly as defined in claim 1 in which the drive electronics include a window gate comparator comprising a high side comparator that includes a peak detect amplifier configured to detect absolute peak amplitudes occurring within echo waveforms.

9. A sealant stream anomaly detecting assembly as defined in claim 8 in which the drive electronics include electronics and software configured to modify echo signals that require either additional gain or attenuation to place their amplitudes within a proper operating range of the window gate comparator.

10. A sealant stream anomaly detecting assembly as defined in claim 1 in which digital control logic is self contained in the drive electronics.

11. A sealant stream anomaly detecting assembly as defined in claim 1 in which:
the digital control logic is configured to examine at least two discrete return echo amplitude periods during each pulse-echo cycle;
the digital control logic controls two independently adjustable temporal sampling window gates for sampling echoes;
one of the adjustable temporal sampling window gates is a manifold window gate configured to provide sonic communication between the transducer and the front wall of the fluid chamber and to detect echoes that reflect from the front wall; and
the other of the adjustable temporal sampling window gates is an anomaly window gate configured to provide sonic communication between the transducer and the back wall of the fluid chamber and to detect echoes that reflect from the back wall of the fluid chamber.

12. A sealant stream anomaly detecting assembly as defined in claim 11 in which the manifold window gate and bubble window gate have independently digitally programmable and adjustable start and width times.

13. A sealant stream anomaly detecting assembly as defined in claim 12 in which the control module is configured to detect the presence of anomalies by detecting diminished back wall echo amplitudes.

14. A sealant stream anomaly detecting assembly as defined in claim 1 in which the digital control logic is configured to provide an adjustable scanning pulse repetition rate of between 1000 and 5000 pulses per second.

15. A sealant stream anomaly detecting assembly as defined in claim 14 in which the pulse-echo intervals are user adjustable.

16. A sealant stream anomaly detecting assembly as defined in claim 1 in which the digital control logic is configured to employ temporal filtering of output signals from the window gate comparator to select only a return echo period of interest and to strip out extraneous echo signals.

17. A sealant stream anomaly detecting assembly as defined in claim 1 in which the digital control logic is configured to cause the transducer to send out a pulse and to measure the amplitude of the returned echo of the pulse within an appropriate temporal window and to compare the amplitude of the returned echo against a comparator threshold value to determine, in each cycle, whether or not the echo amplitude indicates the presence of an anomaly.

18. A sealant stream anomaly detecting assembly as defined in claim 17 in which the comparator threshold value is adjustable.

19. A sealant stream anomaly detecting assembly as defined in claim 1 in which the digital control logic includes a filter counter and is configured to turn on the anomaly indicator when the number of failed pulse-echo cycles equals a preset value of the filter counter.

20. A sealant stream anomaly detecting assembly as defined in claim 19 in which the value of the filter counter is adjustable.

21. A sealant stream anomaly detecting assembly as defined in claim 1 in which the control module includes a user electrical I/O interface configured to accept input signals from and provide output signals to an external controller configured to receive the output signals from the digital control logic and to output signals representing information relating to the number of anomalies detected.

22. A sealant stream anomaly detecting assembly as defined in claim 1 in which the transducer is a semi-custom version of a generic industrial immersion transducer having a pigtail connector modified to displace an electrical connection point away from a main body of the transducer.

23. A sealant stream anomaly detecting assembly as defined in claim 1 in which the control module includes a user serial interface configured to connect the module to a computer to allow stored parameters and diagnostics of system operation to be viewed and adjusted.

24. A sealant stream anomaly detecting assembly as defined in claim 1 in which the control module includes:
a self contained micro controller having resident logic configured to control timing, logic, sample, compare and user interface functions;
an onboard switching power supply configured to generate power and voltage levels that the control module requires for logic and hardware operation, the onboard switching power supply also being configured to generate a boost voltage supply for transducer pulse excitation;
an ultrasonic pulse driver configured to interface between the micro controller and the boost voltage supply and to store and discharge energy to the transducer;
circuit elements configured to isolate and condition signals and to convert waveforms to digital format for further processing by the micro controller; and
an ultrasonic transducer interface configured to connect the control module to the transducer.

25. A sealant stream anomaly detecting assembly as defined in claim 1 in which the drive elctronics include isolated analog and digital and chassis reference grounds.

26. A method for detecting anomalies in a high-pressure sealant stream, the method including the steps of:

providing a manifold defining a sensing chamber in a fluid channel;

providing an ultrasonic transducer, associated drive electronics and an anomaly indicator, the manifold including an acoustic coupling disposed between the transducer and a back wall of the sensing chamber;

connecting the ultrasonic transducer and associated drive electronics to the sensing chamber and connecting the anomaly indicator to the drive electronics;

passing through the sensing chamber a fluid to be inspected for the presence of anomalies;

actuating the drive electronics to operate the transducer and detect anomalies in the fluid passing through the sensing chamber; actuating the anomaly indicator to indicate to an operator and/or supervisory controller when the transducer and drive electronics detect an anomaly in the fluid passing through the sensing chamber; and verifying the adequacy of the acoustic coupling by programming the drive electronics to provide a temporal sampling window gate that provides sonic communication between the transducer and an interface boundary between the acoustic coupling and the fluid chamber and detects echoes that reflect from that interface boundary.

27. The method of claim 26 including the additional steps of:

monitoring the status of the transducer and associated connecting cables for an open or short circuit condition; and indicating to an operator and/or supervisory controller the presence of such conditions.

28. The method of claim 26 including the additional steps of:

performing an internal check verifying that the pulse driver voltage is at a specified level; and, if not, shutting down the assembly and turning off a "system OK" indicator output.

29. The method of claim 26 in which:

the step of providing an ultrasonic transducer includes providing an industrial immersion transducer having a pigtail connector; and including the additional step of modifying the pigtail electrical connection of the transducer to displace an electrical connection away from a main body of the transducer.

30. The method of claim 26 in which the steps of providing the sensing chamber in a fluid channel includes positioning the fluid manifold assembly as close to the point of fluid discharge as possible.

31. The method of claim 26 in which the step of actuating the drive electronics to operate the transducer and detect anomalies in the fluid passing through the sensing chamber includes:

preprogramming the drive electronics to cause the transducer to repeatedly bounce ultrasonic impulses off a back wall of the sensing chamber at regular intervals; and to then monitor the returned echoes from within the sensing chamber during each pulse-echo cycle looking for anomalous waveform echoes that indicate the presence of anomalies.

32. A method for detecting anomalies in a high-pressure sealant stream, the method including the steps of:

providing a sensing chamber in a fluid channel;

providing an ultrasonic transducer, associated drive electronics and an anomaly indicator;

connecting the ultrasonic transducer and associated drive electronics to the sensing chamber and connecting the anomaly indicator to the drive electronics;

passing through the sensing chamber a fluid to be inspected for the presence of anomalies;

actuating the drive electronics to operate the transducer and detect anomalies in the fluid passing through the sensing chamber;

adjusting the lengths of the intervals between impulses to optimize anomaly detection sensitivity to the flow requirements of a fluid system to be monitored; and actuating the anomaly indicator to indicate to an operator and/or supervisory controller when the transducer and drive electronics detect an anomaly in the fluid passing through the sensing chamber.

33. A method for detecting anomalies in a high-pressure sealant stream, the method including the steps of:

providing a sensing chamber in a fluid channel;

providing an ultrasonic transducer, associated drive electronics and an anomaly indicator;

connecting the ultrasonic transducer and associated drive electronics to the sensing chamber and connecting the anomaly indicator to the drive electronics;

passing through the sensing chamber a fluid to be inspected for the presence of anomalies;

preprogramming the drive electronics to examine at least two discrete return echo amplitude periods during each pulse-echo cycle, the first return echo amplitude period being configured to verify that the transducer is sending and receiving echoes by providing sonic communication with the interface between the acoustic coupling and the fluid chamber, and the second return echo amplitude period being configured to provide sonic communication with a back wall of the sensing chamber such that the drive electronics are able to detect anomalies in the sensing chamber by detecting diminished back wall echo amplitudes;

actuating the drive electronics to operate the transducer and detect anomalies in the fluid passing through the sensing chamber; and actuating the anomaly indicator to indicate to an operator and/or supervisory controller when the transducer and drive electronics detect an anomaly in the fluid passing through the sensing chamber.

34. The method of claim 33 in which;

the step of providing drive electronics includes providing drive electronics configured to detect failed pulse-echo cycles; and the step of actuating the anomaly indicator includes activating an anomaly alarm when the number of failed pulse-echo cycles equals a preset value.

35. A sealant stream anomaly detecting assembly for detecting anomalies such as gas bubbles in a high-pressure sealant stream, the assembly comprising:

an ultrasonic transducer supported adjacent a sensing chamber portion of a fluid channel, the transducer being configured to convert electrical input voltage pulses into ultrasonic acoustic energy pulses and to propagate the acoustic energy pulses into the sensing chamber, the transducer also being configured to receive resulting echo pulses from a back wall of the sensing chamber and to convert the echo pulses into electrical output impulses;

a control module including drive electronics connected to the transducer, the module configured to receive the electrical output impulses from the transducer and to detect diminished and lost echo pulses by comparing the output impulse strength values for a given fluid passing through the sensing chamber to a known output impulse strength value for that same type of fluid having no anomalies;

an anomaly indicator connected to the control module and configured to flag a user in response to a signal from the control module indicating that the assembly has detected an anomaly such as a bubble in a fluid stream passing through the fluid channel; and an acoustic coupling supported between the transducer and the sensing chamber and configured to propagate acoustic energy pulses from the transducer into the sensing chamber while isolating the transducer from fluid passing through the sensing chamber, the acoustic coupling being formed from polyphenylene sulfide (PPS).

36. A sealant stream anomaly detecting assembly for detecting anomalies such as gas bubbles in a high-pressure sealant stream, the assembly comprising:

an ultrasonic transducer supported adjacent a sensing chamber portion of a fluid channel, the transducer being configured to convert electrical input voltage pulses into ultrasonic acoustic energy pulses and to propagate the acoustic energy pulses into the sensing chamber, the transducer also being configured to receive resulting echo pulses from a back wall of the sensing chamber and to convert the echo pulses into electrical output impulses;

a control module including drive electronics connected to the transducer, the module configured to receive the electrical output impulses from the transducer and to detect diminished and lost echo pulses by comparing the output impulse strength values for a given fluid passing through the sensing chamber to a known output impulse strength value for that same type of fluid having no anomalies;

an anomaly indicator connected to the control module and configured to flag a user in response to a signal from the control module indicating that the assembly has detected an anomaly such as a bubble in a fluid stream passing through the fluid channel; and an acoustic coupling supported between the transducer and the sensing chamber and configured to propagate acoustic energy pulses from the transducer into the sensing chamber while isolating the transducer from fluid passing through the sensing chamber, the acoustic coupling including a notch that defines the sensing chamber and channels the fluid for inspection directly through the sensing field of the transducer.

37. A sealant stream anomaly detecting assembly as defined in claim 36 in which the notch that defines the sensing chamber is narrower than a sensing element of the transducer.

* * * * *

UNITED STATES PATENT AND TRADEMARK OFFICE
CERTIFICATE OF CORRECTION

PATENT NO.   : 6,595,035 B1
DATED        : July 22, 2003
INVENTOR(S)  : Myron G. Maley It is certified that error appears in the above-identified patent and that said Letters Patent is hereby corrected as shown below:

Column 4,
Line 10, after "FIG. 1 with" delete "an"

Column 6,
Line 57, after "suitable" delete "a"

Column 7,
Line 2, after "notch in" insert therein -- the --

Column 12,
Lines 48-54, move paragraph at Column 12, lines 48-54 to Column 13, line 3, and replace the paragraph at Column 13, lines 3-9. Then, at Column 12, line 48, insert first full paragraph on page 14 of application Column 13,
Line 67, replace "140625 in 2" with -- . 140625 in 2 --

Column 15,
Line 26, after "equate to" delete "increased' sensitivity" and insert therein -- increased sensitivity --
Line 41, after "circuit" delete "bard" and insert therein -- board --

Column 16,
Line 56, before "#1" delete "AID" and insert therein -- A/D --

Column 17,
Lines 15-25, move paragraph starting with "The Manifold Threshold" before the previous paragraph starting with "The boost status…"

Column 18,
Line 10, after "position" delete "the"
Lines 27 and 32, after "Command-->" delete "Jescso" and insert -- Jesco --

Column 22,
Line 55, after "print f" delete "("[r]")" and insert -- ("\r") --

UNITED STATES PATENT AND TRADEMARK OFFICE
CERTIFICATE OF CORRECTION

PATENT NO.     : 6,595,035 B1
DATED          : July 22, 2003
INVENTOR(S)    : Myron G. Maley It is certified that error appears in the above-identified patent and that said Letters Patent is hereby corrected as shown below:

Column 23,
Line 53, before "PIRZ" delete "bffss" and insert -- btfss --

Column 28,
Line 30, before "(ADZ-CS)" delete "outputlow" and insert -- output_low --
Line 30, before "(AD2_CS)" delete "outputlow" and insert -- output_low --
Line 49, after "ad2" insert -- =0; --

Column 30,
Line 31, after "alarm_latch_timer" insert -- ; --
Line 63, after "isr" insert -- : --

Column 31,
Line 13, delete "skip-;" and insert -- skip--; --

Column 33,
Line 27, delete "boosterrordb-;" and insert -- boosterrordb--; --
Line 45, delete "debouncerawpercent-;" and insert -- debouncerawpercent--; --
Line 54, delete "debouncerawmisses-;" and insert -- debouncerawmisses--; --
Line 66, after "error_level..." delete ""%Iu"" and insert -- %Iu" --

Column 34,
Line 10, after "now..." delete "%Iu" and insert -- %Iu --
Line 11, after "last..." delete "%Iu" and insert -- %Iu --
Line 12, after "pulse..." delete "%Iu" and insert -- %Iu --
Line 18, delete "printcR();" and insert -- printCR(); --
Line 48, after "ad1=%" delete "Id"" and insert -- Id" --
Line 49, after "ad2=%" delete "Id"" and insert -- Id" --
Line 50, after "el=%" delete "Id"" and insert -- Id" --
Line 54, delete "printcR ();" and insert -- printCR(); --

Column 35,
Lines 8 and 16, delete "printcR();" and insert -- printCR(); --

UNITED STATES PATENT AND TRADEMARK OFFICE
CERTIFICATE OF CORRECTION

PATENT NO.   : 6,595,035 B1
DATED        : July 22, 2003
INVENTOR(S)  : Myron G. Maley It is certified that error appears in the above-identified patent and that said Letters Patent is hereby corrected as shown below:

Column 36,
Line 38, delete "if (alarmdebounce)" and insert -- if (alarm_debounce --
Line 66, delete "," and insert -- ; --

Column 40,
Line 64, after "drive" delete "elctronics" and insert therein -- electronics --

Signed and Sealed this

Thirtieth Day of December, 2003

JAMES E. ROGAN
*Director of the United States Patent and Trademark Office*